United States Patent
Danley

(10) Patent No.: US 6,431,747 B1
(45) Date of Patent: Aug. 13, 2002

(54) HEAT FLUX DIFFERENTIAL SCANNING CALORIMETER SENSOR

(75) Inventor: Robert L. Danley, Collingswood, NJ (US)

(73) Assignee: TA Instruments, Inc., New Castle, DE (US)

( * ) Notice: Subject to any disclaimer, the term of this patent is extended or adjusted under 35 U.S.C. 154(b) by 55 days.

(21) Appl. No.: 09/643,870

(22) Filed: Aug. 23, 2000

Related U.S. Application Data

(63) Continuation-in-part of application No. 09/533,949, filed on Mar. 23, 2000, now abandoned.

(51) Int. Cl.[7] .......................... G01K 1/20; G01K 17/04; G01K 17/08; G01N 1/00
(52) U.S. Cl. ............................... 374/10; 374/1; 374/32; 374/33
(58) Field of Search ............................... 374/29, 31, 33, 374/30, 1, 43, 10–12

(56) References Cited

U.S. PATENT DOCUMENTS

| | | |
|---|---|---|
| 3,263,484 A | 8/1966 | Watson et al. |
| 3,732,722 A | 5/1973 | Norem et al. |
| 4,095,453 A | 6/1978 | Woo |
| 4,330,933 A | 5/1982 | Bullinger et al. |
| 4,350,466 A | 9/1982 | Bahr et al. |
| 4,614,721 A | 9/1986 | Goldberg ..................... 436/147 |
| 4,783,174 A | 11/1988 | Gmelin et al. |
| 5,033,866 A | 7/1991 | Kehl et al. |
| 5,224,775 A | 7/1993 | Reading et al. |
| 5,288,147 A | 2/1994 | Schaefer et al. |
| 5,346,306 A | * 9/1994 | Reading et al. ................ 374/10 |
| 5,474,385 A | * 12/1995 | Reading ....................... 374/11 |
| 5,599,104 A | * 2/1997 | Nakamura et al. ............. 374/12 |
| 5,813,763 A | * 9/1998 | Plotnikov et al. .............. 374/11 |
| 5,842,788 A | * 12/1998 | Danley et al. ................. 374/12 |
| 6,079,873 A | * 6/2000 | Cavicchi et al. ............... 374/10 |
| 6,146,012 A | * 11/2000 | Nakamura et al. ............. 374/10 |
| 6,170,984 B1 | * 1/2001 | Schawe et al. ................ 374/10 |
| 6,200,022 B1 | * 3/2001 | Hammiche et al. ............ 374/46 |

FOREIGN PATENT DOCUMENTS

| | | | |
|---|---|---|---|
| DE | 30 49 105 A | 7/1982 | .......... G01N/25/20 |
| EP | 0701122 | 3/1996 | |
| EP | 0 701 122 | 3/1996 | .......... G01N/25/48 |
| JP | 02082145 | * 3/1990 | |
| WO | WO 95/33199 | 7/1995 | |

OTHER PUBLICATIONS

"Differential Scanning Calorimetry an Introduction for Practioners", G. Hohne, W. Hemminger, and H.J. Flammersheim (Springer–Verlag 1996).

* cited by examiner

Primary Examiner—Diego Gutierrez
Assistant Examiner—Gail Verbitsky
(74) Attorney, Agent, or Firm—Shaw Pittman LLP

(57) ABSTRACT

A sensor for a heat flux differential scanning calorimeter in which one absolute temperature measurement and two differential temperature measurements are used. The sensor is calibrated and used based on a four-term model heat flow equation. The calibration is carried out in two experiments which are used to calculate the sensor thermal resistance for the sample and reference positions, respectively, and the sensor heat capacity for the sample and reference positions, respectively. Differential scanning calorimeters using this sensor exhibit improved resolution, improved baseline performance and improved dynamic response.

83 Claims, 10 Drawing Sheets

HEAT FLUX DIFFERENTIAL SCANNING CALORIMETER SENSOR

The present application is a continuation-in-part of U.S. patent application Ser. No. 09/533,949, filed Mar. 23, 2000, now abandoned, which is incorporated herein by reference, and claims priority from the filing date of that application.

BACKGROUND

1. Field of the Invention

The present invention relates to a thermal analysis instrument, and more particularly, to a differential scanning calorimeter.

2. Background of the Invention

Heat Flux Differential Scanning Calorimeters (DSCs) have a sensor which measures the temperature difference between a sample and a reference position. A sample to be analyzed is loaded into a pan and placed on the sample position of the sensor and an inert reference material is loaded into a pan and placed on the reference position of the sensor (an empty pan is often used as the reference). The sensor is installed in an oven whose temperature is varied dynamically according to a desired temperature program. The temperature program for conventional DSCs typically includes combinations of linear temperature ramps and constant temperature segments. Modulated DSC uses a temperature program in which periodic temperature modulations are superimposed on linear ramps. Modulated DSCs are described in U.S. Pat. No. 5,224,775, which is incorporated by reference herein. During the dynamic portion of the DSC experiment, a differential temperature is created between the sample and reference positions on the sensor. The temperature difference is the result of the difference between the heat flow to the sample and the heat flow to the reference. Because the temperature difference is proportional to the difference in heat flow to the sample as compared to the reference, that differential temperature may be used to measure the heat flow to the sample.

FIG. 1 shows a thermal network model that may be used to represent heat flux in certain DSC sensors. $T_o$ is the temperature at the base of the sensor near its connection to the oven, $T_s$ is the temperature of the sample position of the sensor and $T_r$ is the temperature of the reference position of the sensor. $R_s$ and $R_r$ represent the thermal resistance between the base of the sensor and the sample and reference positions, respectively. $C_s$ and $C_r$ represent the thermal capacitance of the sample and reference portions of the sensor. Thermal capacitance is the product of mass and specific heat and is a measure of the heat storage capacity of a body, i.e., it is the heat capacity of the body. The heat flow to the sample and the reference are $q_s$ and $q_r$, respectively. It should be understood that $q_s$ and $q_r$ include heat flow to sample and reference pans. During the execution of a thermal program the base temperature of the sensor $T_o$ follows the thermal program. The temperatures at the sample and reference positions, $T_s$ and $T_r$, lag the base temperature $T_o$ due to heat flowing to the sample and to the reference and heat which is stored within the sensor in sensor sample thermal capacitance $C_s$ and sensor reference thermal capacitance $C_r$.

Performing a heat flow balance on the sample side of the sensor yields a heat flow $$q_s = \frac{T_o - T_s}{R_s} - C_s \cdot \frac{dT_s}{d\tau}$$

trough the sensor sample thermal resistance $R_s$ minus the heat stored in $C_s$. Similarly, a heat balance on the reference side of the sensor gives $$q_r = \frac{T_o - T_r}{R_r} - C_r \cdot \frac{dT_r}{d\tau}$$

through sensor reference thermal resistance $R_r$ minus the heat stored in $C_r$. In the equations herein, $\tau$ represents time.

The desired quantity (the differential heat flow to the sample with respect to the reference) is the difference between the sample and reference heat flows:

$$q = q_s - q_r$$

Substituting for $q_s$ and $q_r$ yields:

$$q = \frac{T_o - T_s}{R_s} - C_s \cdot \frac{dT_s}{d\tau} - \frac{T_o - T_r}{R_r} + C_r \cdot \frac{dT_r}{d\tau}$$

Substituting the following expressions for two temperature differences in a differential scanning calorimeter, $$\Delta T = T_s - T_r$$

$$\Delta T_o = T_o - T_s$$

where $\Delta T$ is the temperature difference between the sample and the reference and $\Delta T_o$ is the temperature difference between the sample and a position at the base of the sensor, results in the DSC heat flow equation:

$$q = \Delta T_o \cdot \left( \frac{R_r - R_s}{R_r \cdot R_s} \right) - \frac{\Delta T}{R_r} + (C_r - C_s) \cdot \frac{dT_s}{d\tau} - Cr \cdot \frac{d\Delta T}{d\tau}$$

The DSC heat flow equation has 4 terms. The first term accounts for the effect of the difference between the sensor sample thermal resistance and the sensor reference thermal resistance. The second term is the conventional DSC heat flow. The third term accounts for the effect of the difference between the sensor sample thermal capacitance and the sensor reference thermal capacitance. The fourth term accounts for the effect of the difference between the heating rates of the sample and reference sides of the DSC. Conventionally, when this equation is applied to the DSC heat flow, the first and third terms are zero because $R_s$ and $R_r$ are assumed to be equal and $C_s$ and $C_r$ are also assumed to be equal.

In reality, because of imprecision in the manufacturing process, sensors are not perfectly balanced. This imbalance contributes to baseline heat flow deviations that may be significant. The first and third terms of the four-term heat flow equation account for the thermal resistance and thermal capacitance imbalances, respectively. The fourth term is generally very nearly equal to zero, except when a transition is occurring in the sample (for instance, during a melt), or during a Modulated DSC experiment. Usually, the heat flow signal is integrated over the area of the transition to obtain the total energy of the transition. Because the fourth term does not contribute to the area of the integration, it has been ignored in the prior art. However, it may contribute significantly to the shape of the heat flow curve during a transition.

Therefore, including the fourth term improves the dynamic response of the heat flow curve. Also, as noted by Hohne, et. al. in "Differential Scanning Calorimetry: An Introduction for Practitioners," (Springer-Verlag, 1996), the fourth term cannot be ignored and must be taken into account when partial integration of the transition peak is performed, e.g., in kinetic investigations for purity determinations. When the fourth term is included, the onset of a transition is sharper and the return to baseline heat flow when the transition is over is more rapid.

Because the resolution of a DSC is its ability to separate transitions that occur in a sample within a small temperature interval, and this is determined essentially by how quickly the heat flow signal returns to baseline after a transition is complete, including the fourth term of the DSC heat flow equation improves the resolution of the DSC sensor by increasing the return to baseline of the heat flow signal after a transition is complete.

The four-term heat flow equation has long been known in the art of differential scanning calorimetry. It can only be applied to heat flux DSC sensors that satisfy certain criteria. The structure of the sensor must be such that the thermal network model correctly represents the dynamic thermal behavior of sensor. Ideally, the sample and reference portions of the sensor should be absolutely independent, i.e., a transition that occurs on the sample side would not have any effect on the reference temperature. Typically, heat flux DSC sensors of the disk type as disclosed in U.S. Pat. No. 4,095,453 to Woo, U.S. Pat. No. 4,350,446 to Johnson, U.S. Pat. No. 5,033,866 to Kehl, et. al. and U.S. Pat. No. 5,288,147 to Schaefer, et. al. cannot use the four-term heat flow equation, because the sample and reference temperature are not independent, and because the four-term heat flow equation does not accurately represent the dynamic thermal behavior of those sensors.

A quantitative measure of the independence of prior art heat flux sensors can be obtained by a simple experiment: for example, if a sample of indium is placed on the reference position of a prior art sensor such as, for example, the type disclosed in U.S. Pat. No. 4,095,453 to Woo, and the sample is heated through the melt, in one exemplary experiment the deviation of the temperature of the sample position observed was observed to be 13.4% of the deviation that would have been obtained if the indium sample had been placed on the sample position. In an ideal instrument, that deviation would have been zero.

U.S. Pat. No. 5,599,104 to Nakamura, et. al. discloses a heat flux DSC sensor that uses two temperature difference measurements. However, these measurements are applied in a different manner using a different heat flow equation and the configuration of the differential temperature measurements is not suitable for use with the four-term heat flow equation. Specifically, Nakamura cannot use the four-term equation because the two temperature differences measured in Nakamura are not suitable for use in the four-term DSC the equation.

SUMMARY OF THE INVENTION

The present invention is a differential scanning calorimeter sensor that measures the differential heat flow to the sample based upon a single absolute temperature measurement and two differential temperature measurements. Differential scanning calorimeters of the present invention have substantially improved resolution over conventional instruments, with an empty-cell heat flow that is much closer to zero than that obtained in conventional instruments.

Temperature Measurements

In the present invention, the differential heat flow to the sample with respect to the reference is calculated from measurements of the absolute temperature of the base of the sensor, the differential temperature between the sample position and the base of the sensor, and the differential temperature between the sample and reference positions. The differential temperatures are measured using a sample area temperature detector and a reference area temperature detector.

The base temperature detector (which measures the temperature of the base of the sensor near its connection to the oven) is used to control the oven temperature. The sample temperature is measured by measuring the difference between the sample temperature and the base temperature, and subtracting that difference from the base temperature to obtain the sample temperature, i.e., the sample temperature is obtained from $T_s=T_o-\Delta T_s$. By making a single absolute temperature measurement, $T_o$ and two differential temperature measurements, any relative errors in absolute temperature measurements due to differences in temperature sensors are eliminated. Also, this structure minimizes the drift of sample temperature during isothermal segments.

The sensor constructed according to the present invention exhibits improved independence between the sample and reference positions. For example, whereas in the exemplary experiment described in the background section, in a prior art heat flux instrument a deviation in the temperature of the sample position of 13.4% was observed when a sample of indium is placed on the reference position and heated through the melt, with the present invention, in an exemplary experiment with the present invention that deviation is only about 1.4%, i.e., the present invention exhibits an improvement by about an order of magnitude over the prior art instruments. Thus sensors constructed according to the present invention are "effectively independent," because they exhibit a temperature deviation at the sample position when an indium sample is placed on the reference position of less than about 1.5% of the temperature deviation at the sample position when an indium sample is placed on the sample position.

Calibration

In a first preferred embodiment, the differential scanning calorimeter of the present invention is calibrated by running two separate experiments. These experiments determine the four sensor thermal parameters, $C_s$ (the sensor sample thermal capacitance), $C_r$ (the sensor reference thermal capacitance), $R_s$ (the sensor sample thermal resistance) and $R_r$ (the sensor reference thermal resistance) experimentally, and thus calibrate the heat flow sensor.

The first experiment is performed with an empty DSC cell. The DSC cell is first held at an isothermal temperature that is below the temperature range of the calibration, for a time segment sufficient to ensure complete equilibration of the sensor. The DSC cell is then heated at a constant heating rate to a temperature above the temperature range of the calibration, and then held at that temperature for another isothermal segment, for a time segment sufficient to ensure equilibration of the sensor at that temperature. This first experiment is used to calculate the sample and reference time constants as a function of temperature over the calibrated temperature range.

The heat flow to the sample and the heat flow to the reference should be zero (since the DSC cell is empty). Accordingly, if $q_s$ and $q_r$ are set equal to zero in the heat balance equations for the sample and reference sides of the sensor, the time constants for the sample and reference are given by:

$$\tau_s = C_s R_s = \frac{\Delta T_o}{\left(\frac{dT_s}{d\tau}\right)} \quad \text{and}$$

$$\tau_r = C_r R_r = \frac{\Delta T_o + \Delta T}{\frac{dT_s}{d\tau} - \frac{d\Delta T}{d\tau}}$$

respectively. These results are stored as a function of temperature.

The second experiment uses a pair of calibration samples. The calibration samples may have the same mass, or may have different masses. Preferably, the calibration samples are sapphire samples, preferably weighing 25 mg or more. Other reference materials with well-known specific heats and no transitions in the temperature range of the calibration may be used instead of sapphire (in which case $C_{sapph}$ would be replaced in the following equations by $C_{mat}$ where $C_{mat}$ is the specific heat of the other reference material).

The sample and reference heat flows from the heat balance equations are set as follows:

$$q_s = m_s \cdot C_{sapph} \cdot \frac{dT_{ss}}{d\tau}$$

$$q_r = m_r \cdot C_{sapph} \cdot \frac{dT_{rs}}{d\tau}$$

where $m_s$, $m_r$ are the masses of the sample and reference sapphires, respectively, $C_{sapph}$ is the specific heat of sapphire and $T_{ss}$ and $T_{rs}$ are the temperatures of the sample and reference sapphire.

Assume:

$$\frac{dT_{ss}}{d\tau} = \frac{dT_s}{d\tau} \quad \text{and} \quad \frac{dT_{rs}}{d\tau} = \frac{dT_r}{d\tau}$$

Substituting for $q_s$ and $T_s$ in the sample heat balance equation and solving for the sensor sample thermal capacitance $C_s$:

$$C_s = \frac{m_s \cdot Csapph}{\frac{\Delta T_o}{\left(\frac{dT_s}{d\tau}\right) \cdot \tau_s} - 1}$$

Substituting for $q_s$ and $\tau_r$ in the reference heat balance equation and solving for the sensor reference thermal capacitance $C_r$:

$$C_r = \frac{m_r \cdot C_{sapph}}{\frac{\Delta T_o + \Delta T}{\left(\frac{dT_s}{d\tau} - \frac{d\Delta T}{d\tau}\right) \cdot \tau_r} - 1}$$

The results from the second experiment using sapphire (or another well-known calibration material; if the calibration material is not sapphire, then replace $C_{sapph}$ in the equations herein with $C_{mat}$, the specific heat of the calibration material) using the time constants for DSC cell obtained in the first experiment are then used to calculate the sample and reference sensor heat capacities as a function of temperature. Finally, the sensor sample and reference thermal resistances are calculated from the time constants and the sensor thermal capacitances:

$$R_s = \frac{\tau_s}{C_s} \quad \text{and} \quad R_r = \frac{\tau_r}{C_r}$$

A second preferred embodiment is similar to the first embodiment, but uses sapphire (or another material with a well-known heat capacity and no transitions in the temperature range of interest) calibration samples in both the first and the second calibration experiments. The calibration equations and their derivation for this embodiment are described below.

Accordingly, the present invention is a differential scanning calorimeter that provides improved resolution by accounting for all four terms of the heat flow equation. The present invention also provides a differential scanning calorimeter with an empty-cell heat flow much closer to zero than conventional instruments. Another advantage of the present invention is that it provides a more complete and correct measure of the heat flow to the sample.

Additional features and advantages of the invention well be set forth in the description which follows, and in part will be apparent from the description, or may be learned by practice of the invention. The objectives and other advantages of the invention will be realized and attained by the structure particularly pointed out in the written description and claims as well as the appended drawings.

DETAILED DESCRIPTION OF THE INVENTION

Temperature Measurements

Figure 2:
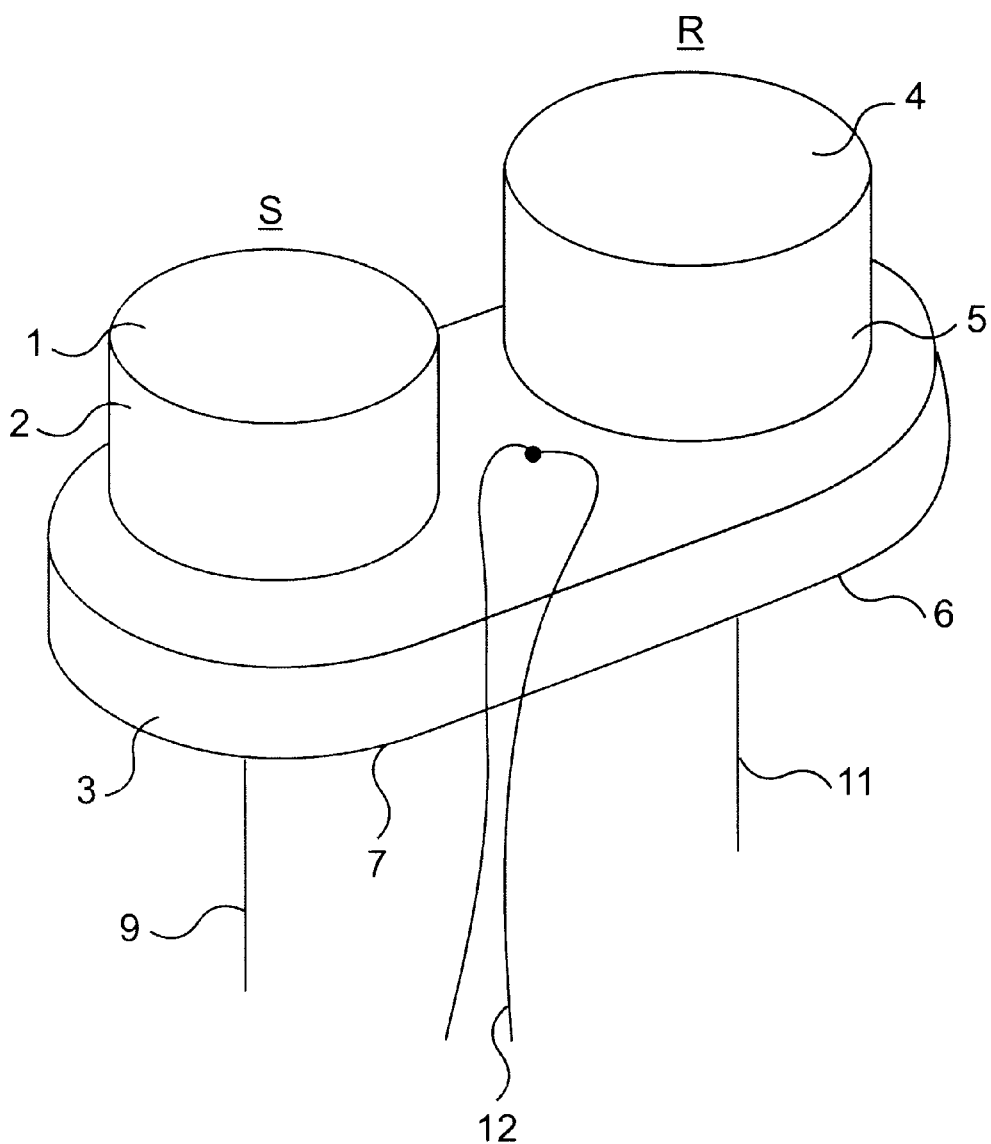
FIG. 2 is an isometric view of an embodiment of the sensor of the present invention.

FIG. 2 is a schematic diagram of an overall view of a preferred embodiment of a heat flux DSC sensor according to the present invention. The sample is loaded in a pan and placed on the sample platform 1. Sample platform 1 is a thin flat circular disk that is attached to the thin wall cylindrical tube 2, which is also joined to the base 3. The reference is loaded in a pan placed on the reference platform 4. Reference platform 4 is a thin flat circular disk that is attached to thin wall cylindrical tube 5, which is also joined to the base 3. The platforms, tubes and base (items 1 through 5) are integral parts of the sensor body 6 which is made of constantan, the negative element of a type E thermocouple. The thin wall tube portions 2 and 5 of the sensor body are the principal contributors to the thermal resistances $R_s$ and $R_r$ of the DSC sensor. The underside of the base 7 is a flat surface. This surface is the mounting surface of the sensor used to install the sensor in the DSC oven.

A typical sample thin wall cylindrical tube 2 and reference thin wall cylindrical tube 5 have a height of 0.09 inches, a diameter of 0.187 inches, and a wall thickness of 0.005 inches. The sample platform thickness is also 0.005 inches. Thus the cross sectional area of the tube itself (i. e., the tube's circumference times its thickness) is about 0.00284 square inches, such that the aspect ratio (the ratio of the height of the cylinder to its cross-sectional area) is about $31.5$ inches$^{-1}$. The aspect ratio should preferably range from 25 to 35, in order to obtain both good resolution and good sensitivity. The sensor's sensitivity may be increased (at a cost to its resolution), by increasing the height of the cylinder, to, for example, 0.3–0.5 inches. Alternatively, the sensor's resolution may be increased (at a cost to its sensitivity), by reducing the cylinder height to, for example, 0.02 to 0.04 inches.

Figure 3:
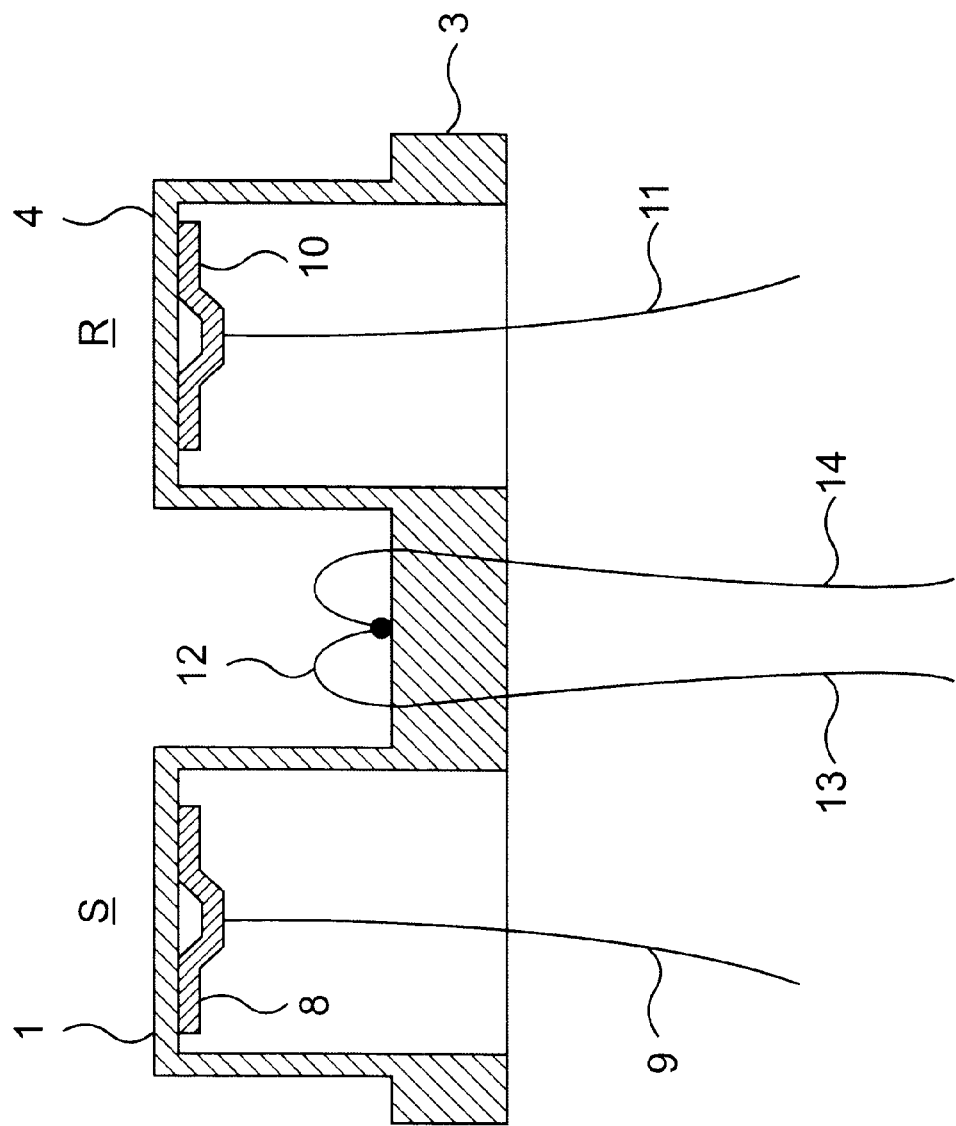
FIG. 3 is a cross sectional view of an embodiment of the sensor according to the present invention.
Figure 3A:
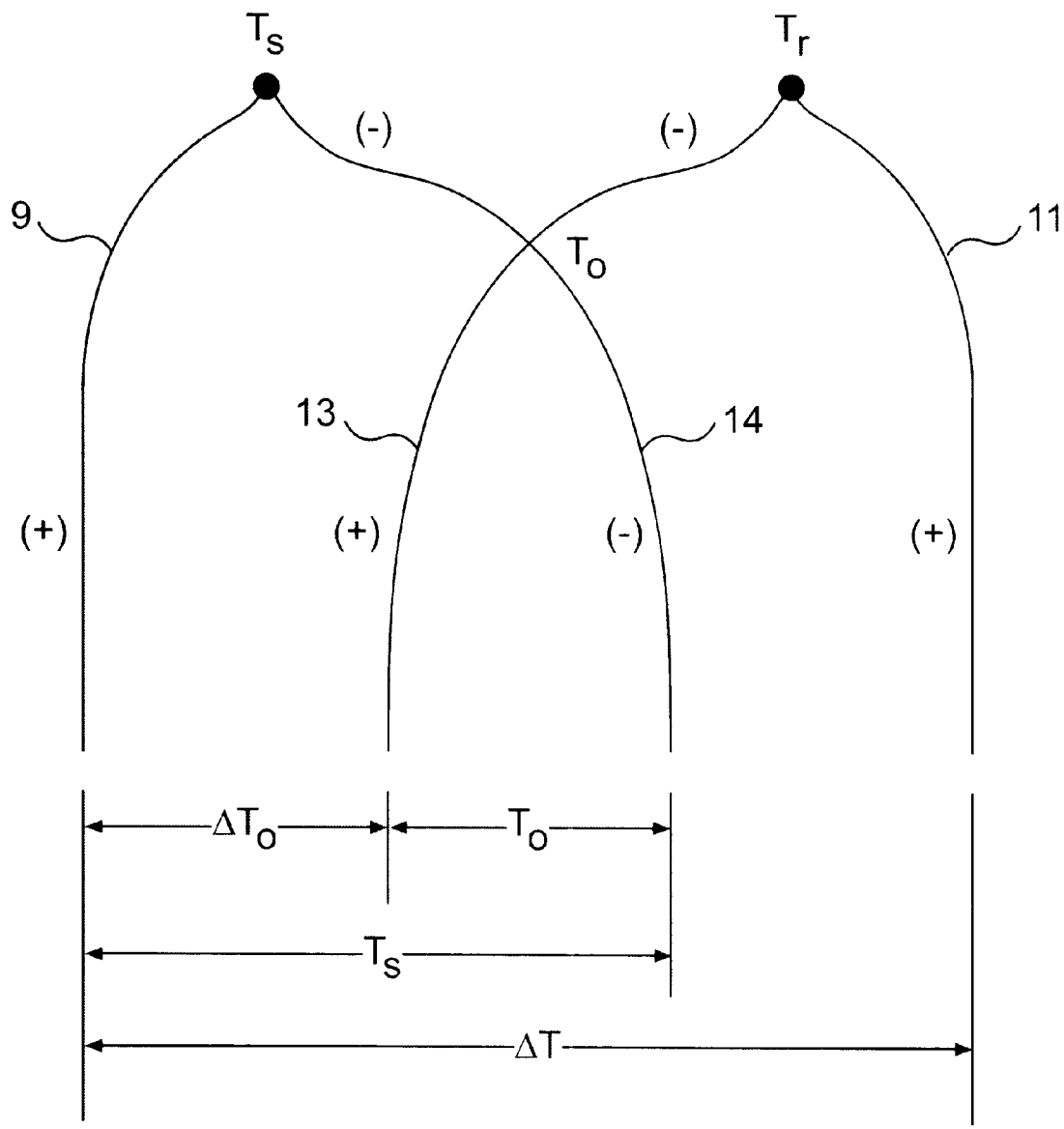
FIG. 3a is an electrical schematic showing how the thermocouples of FIG. 3 are used to measure the absolute and differential temperatures in the present invention.

FIG. 3 is a schematic diagram of a cross sectional view through the DSC sensor, taken at a plane perpendicular to and passing through the centers of the sample and reference platforms. FIG. 3a is the corresponding electrical thermocouple arrangement. A sample area temperature detector 8 is welded concentrically to the underside of the sample platform 1. The area temperature detector is a thin circular disk of chromel that is the thermoelectrically positive element of a type E thermocouple. At the center is a depressed portion to which a chromel wire 9 is welded. The sample area temperature detector 8 is welded to the underside of the sample platform 1 at sixteen places equally spaced in a circular pattern concentric to the sample area detector 8 and sample platform 1, thus forming sixteen thermoelectric junctions in parallel between the constantan sample platform 1 and the sample area temperature detector 8.

A reference area temperature detector 10 is welded concentrically to the underside of the reference platform 4. The reference area temperature detector 10 is a thin circular disk of chromel that is the thermoelectrically positive element of a type E thermocouple. At the center is a depressed portion to which a chromel wire 11 is welded. The reference area temperature detector 10 is welded to the underside of the reference platform 4 at sixteen places equally spaced in a circular pattern concentric to the reference area temperature detector 10 and reference platform 4, thus forming sixteen thermoelectric junctions in parallel between the constantan reference platform 4 and the reference area temperature detector 10. A type E thermocouple 12 is welded to the center of the top surface of the base 3. Lead wire 13 is the chromel and lead wire 14 is the constantan element of the type E thermocouple.

FIG. 3a is a schematic representation of the thermocouple configuration, showing how the voltages representing $\Delta T_o$, $T_s$ and $\Delta T_o$ are measured. The (+) signs indicate the chromel leads and the area detectors. The (−) signs indicate the constantan sensor body and the constantan leads. As shown in FIG. 3a, the voltage representing the differential temperature $\Delta T$ between the sample and the reference is measured between chromel lead wire 9 and chromel lead wire 11. The voltage representing the differential temperature $\Delta T_o$ between the sample and the base is measured between chromel lead wires 9 and 13. The sixteen parallel thermocouple junctions between area detectors 8 and 10 and sample and reference platforms 1 and 4, respectively, allow the measurement of the difference between the average temperatures of the sample and reference platforms as described in U.S. Pat. No. 4,095,453, which is incorporated by reference herein. Area detector 8 also allows measurement of the difference between the average temperature of the sample platform and the temperature at the base of the sensor. The area detectors and associated parallel thermocouples reduce the sensitivity of the $\Delta T$ and $\Delta T_o$ measurements to any variations in the position of the pans upon the sensor, as well as the sensitivity due to variations in the contact resistance between the pan and the sensor. Type E thermocouple 12 is used to measure $T_o$, the temperature at the base of the sensor. As shown in FIG. 3a, the voltage representing this temperature appears between lead wires 13 and 14. The sample temperature representing $T_s$ is obtained by combining voltages representing $T_o$ and $\Delta T_o$ to obtain the voltage representing $T_s$ that would appear between lead wires 9 and 14. While the preferred embodiment discloses a structure using combinations of the thermoelectric materials constantan and chromel, one of ordinary skill in the art would recognize that other thermocouple materials could be used to make the same measurements and achieve the same results.

Those skilled in the art would also recognize that there are numerous other configurations whereby a single temperature measurement and two differential measurements could be used with a slightly different four-term heat flow equation to obtain the same result. There are three possible choices for the temperature measurement: the sample platform temperature $T_s$, the reference platform temperature $T_r$ and the sensor base temperature $T_o$. Each of these can be used with any two of the three differential temperature measurements to achieve the same result. Thus, in the preferred embodiment described above, the base temperature $T_o$ is used for the absolute temperature measurement, with differential temperature measurements $T_o-T_s$ and $T_s-T_r$. The base temperature $T_o$ could also be used with differential measurements $T_o-T_s$ and $T_o-T_r$ or with $T_s-T_r$ and $T_o-T_r$. The reference temperature $T_r$ can be used as the absolute temperature measurement with differential temperature measurements $T_s-T_r$ and $T_o-T_r$ or with $T_o-T_r$ and $T_o-T_s$ or with $T_s-T_r$ and $T_o-T_s$. The sample temperature $T_s$ can be used as the absolute temperature measurement with $T_o-T_s$ and $T_s-T_r$, or with $T_o-T_s$ and $T_o-T_r$ or with $T_o-T_r$ and $T_s-T_r$. Thus, there are eight additional configurations that could give the same information if the four-term heat flow equation is rewritten accordingly. All nine of the possible configurations are within the scope of the present invention.

First Preferred Method for Determining Sensor Thermal Parameters

Preferably, the sensor is calibrated prior to use. The sensor is calibrated by determining the values of sensor thermal parameters $C_s$, $C_r$, $R_s$ and $R_r$.

As described above, in a first preferred embodiment of the present invention, the sensor is calibrated by performing two sequential measurements, the first with an empty DSC cell, and the second with a sapphire sample in the sample position and another sapphire sample in the reference position. Preferably, the sapphire samples should each weigh at least 25 mg.

As described above, for the first calibration experiment a thermal program starting with an isothermal temperature segment at a temperature below the calibration range, followed by a constant heating rate temperature ramp, and ending with an isothermal segment above the calibration range is applied to the empty DSC cell. Preferably, the heating rate used during calibration should be the same as that used for subsequent experiments. Preferably, the temperature range of the calibration equals or exceeds the temperature range of the subsequent experiments.

The sample time constant as a function of temperature is then given by:

$$\tau_s = C_s R_s = \frac{\Delta T_o}{\left(\frac{dT_s}{d\tau}\right)}$$

and the reference time constant is given by:

$$\tau_r = C_r R_r = \frac{\Delta T_o + \Delta T}{\frac{dT_s}{d\tau} - \frac{d\Delta T}{d\tau}}$$

The results from the empty DSC experiment are used to calculate and store the time constants as a function of sample temperature.

As described above, for the second calibration experiment, a pair of sapphire calibration samples is placed on the sample and reference positions of the sensor. The thermal program that was used for the empty DSC experiment is then applied to the DSC cell.

As shown above, the sensor sample thermal capacitance is given by:

$$C_s = \frac{m_s \cdot C_{sapph}}{\frac{\Delta T_o}{\left(\frac{dT_s}{d\tau}\right) \cdot \tau_s} - 1}$$

and the sensor reference thermal capacitance is given by:

$$C_r = \frac{m_r \cdot C_{sapph}}{\frac{\Delta T_o + \Delta T}{\left(\frac{dT_s}{d\tau} - \frac{d\Delta T}{d\tau}\right) \cdot \tau_r} - 1}$$

These equations are used with the time constants from the empty DSC cell experiments to calculate the sample and reference sensor heat capacities as a function of temperature. Finally, the sensor thermal resistances are computed from the time constants and sensor thermal capacitances:

$$R_s = \frac{\tau_s}{C_s} \text{ and } R_r = \frac{\tau_r}{C_r}$$

The thermal capacitances and resistances are used in the DSC heat flow calculation either as tabular data that are interpolated between points or the data may be fitted with a polynomial. Generally, the thermal capacitance and resistance data are smooth and well behaved so that a low order polynomial fit gives sufficient precision.

Second Preferred Method for Determining Sensor Parameters

A second preferred method for calibrating the DSC sensor is to perform two sequential DSC scans with samples in both scans, using, e.g., sapphire samples. The sample masses on both sample and reference sides must be different for the two scans.

As for the first embodiment, we assume the heating rates of the samples are the same as the heating rates of the sample and reference sides of the sensor.

For the sample side, the heat flows are given by:

$$q_{s1} = m_{s1} \cdot C_{sapph} \cdot \frac{dT_{s1}}{d\tau}$$

$$q_{s2} = m_{s2} \cdot C_{sapph} \cdot \frac{dT_{s2}}{d\tau}$$

The numeric subscripts indicate scans 1 and 2.

The heat balance equation for the sample side for scans 1 and 2 are then:

$$q_{s1} = \frac{\Delta T_{o1}}{R_s} - C_s \cdot \frac{dT_{s1}}{d\tau}$$

$$q_{s2} = \frac{\Delta T_{o2}}{R_s} - C_s \cdot \frac{dT_{s2}}{d\tau}$$

Solving the heat balance equations simultaneously gives, $$C_s = \frac{\Delta T_{o1} \cdot q_{s2} - \Delta T_{o2} \cdot q_{s1}}{\Delta T_{o2} \frac{dT_{s1}}{d\tau} - \Delta T_{o1} \frac{dT_{s2}}{d\tau}}$$

$$R_s = \frac{\Delta T_{o2} \cdot \frac{dT_{s1}}{d\tau} - \Delta T_{o1} \cdot \frac{dT_{s2}}{d\tau}}{q_{s2} \cdot \frac{dT_{s1}}{d\tau} - q_{s1} \cdot \frac{dT_{s2}}{d\tau}}$$

For the reference side:

$$q_{r1} = m_{r1} \cdot C_{sapph} \cdot \frac{dT_{r1}}{d\tau}$$

$$q_{r2} = m_{r2} \cdot C_{sapph} \cdot \frac{dT_{r2}}{d\tau}$$

The heat balance equations for the reference side for samples 1 and 2 are:

$$q_{r1} = \frac{T_{o1} - T_{r1}}{R_r} - C_r \cdot \frac{dT_{r1}}{d\tau}$$

$$q_{r2} = \frac{T_{o2} - T_{r2}}{R_r} - C_r \cdot \frac{dT_{r2}}{d\tau}$$

Substituting as above:

$$q_{r1} = \frac{\Delta T_{o1} + \Delta T_1}{R_r} - C_r \cdot \left(\frac{dT_{s1}}{d\tau} - \frac{d\Delta T_1}{d\tau}\right)$$

$$q_{r2} = \frac{\Delta T_{o2} + \Delta T_2}{R_r} - C_r \cdot \left(\frac{dT_{s2}}{d\tau} - \frac{d\Delta T_2}{d\tau}\right)$$

Solving simultaneously gives:

$$R_r = \frac{(\Delta T_{o2} + \Delta T_2) \cdot \left(\frac{dT_{s1}}{d\tau} - \frac{d\Delta T_1}{d\tau}\right) - (\Delta T_{o1} + \Delta T_1) \cdot \left(\frac{dT_{s2}}{d\tau} - \frac{d\Delta T_2}{d\tau}\right)}{q_{r2} \cdot \left(\frac{dT_{s1}}{d\tau} - \frac{d\Delta T_1}{d\tau}\right) - q_{r1} \cdot \left(\frac{dT_{s2}}{d\tau} - \frac{d\Delta T_2}{d\tau}\right)}$$

-continued $$C_r = \frac{(\Delta T_{o1} + \Delta T_1) \cdot q_{r2} - (\Delta T_{o2} + \Delta T_2) \cdot q_{r1}}{(\Delta T_{o2} + \Delta T_2) \cdot \left(\frac{dT_{s1}}{d\tau} - \frac{d\Delta T_1}{d\tau}\right) - (\Delta T_{o1} + \Delta T_1) \cdot \left(\frac{dT_{s2}}{d\tau} - \frac{d\Delta T_2}{d\tau}\right)}$$

Thus, using the results from two DSC scans with samples with different masses on both the sample and reference sides, the sensor thermal parameters can be computed. Note that one of the two calibration experiments may be performed with an empty DSC, in which case $m_{sl}$ and $m_{rl}$ are zero, and $q_s$ and $q_r$ are also zero (this actually reduces to the first preferred calibration method, i.e., the first method is just a special case of the second method with $m_{sl}=M_{rl}=0$). Alternatively, the same samples could be used in the two calibration experiments, using substantially different heating rates (i.e., the higher heating rate would be 40% above the lower heating rate) between the first and the second experiment.

The DSC Enclosure

The DSC sensor measures the differential heat that flows through the DSC sensor between the sample platform and the DSC enclosure, with respect to the heat that flows through the DSC sensor between the reference platform and the DSC enclosure. However, a small amount of heat flows directly between the sample and reference platforms and the DSC enclosure by heat conduction through the gas, by radiation exchange, and by convection.

Such extraneous heat flows between the sample and reference platforms and the enclosure are not measured and hence, especially to the extent that the extraneous heat flows from the sample platform are not balanced by the extraneous heat flows from the reference platform, contribute to errors in the differential heat flow measurement. The magnitude of this error depends upon the variation of temperature within the DSC enclosure. Increased uniformity of temperature within the enclosure reduces the overall extraneous heat flow generally, and also reduces the difference between the extraneous heat flow from the sample platform and the extraneous heat flow from the reference platform.

In particular, the lid of the DSC enclosure is an important contributor to non-uniformity within the enclosure, because it exchanges heat with the insulation surrounding the enclosure (which in turn exchanges heat with the DSC cell surroundings) and because it has relatively poor thermal contact with the body of the enclosure (because it must be easily removed). Thus, the temperature of the lid may be substantially different from the temperature of the body of the enclosure, and this non-uniformity is responsible for the greatest portion of the extraneous heat flow.

Figure 3B:
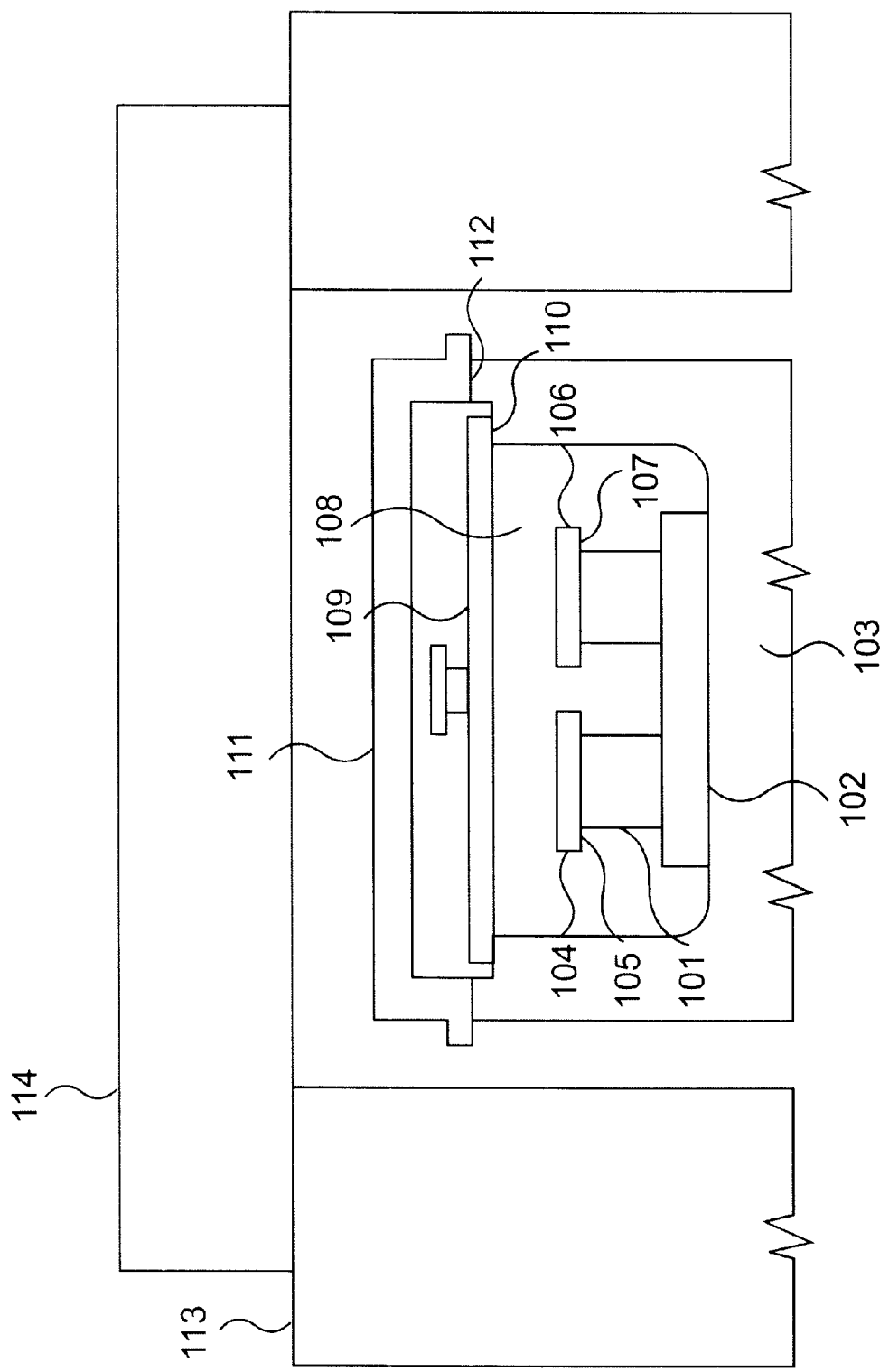
FIG. 3b is a schematic diagram of a cross-section of the DSC cell assembly for a preferred embodiment of the present invention.

In a preferred embodiment of the present invention, shown in FIG. 3b, non-uniformity within the DSC enclosure is greatly reduced by adding a second outer lid that encloses the first inner lid and contacts the body of the DSC enclosure. In this embodiment, heat is exchanged between the insulation surrounding the enclosure and the outer lid. This eliminates heat flow through the DSC enclosure lid, greatly reducing the temperature difference between the body and the lid of the DSC enclosure and substantially reducing the extraneous heat flow.

FIG. 3b is a schematic diagram of a cross section through the upper portion of the DSC cell assembly (the lower portion is omitted for clarity). The DSC sensor of the present invention 101 is mounted to the lower surface 102 of the body 103 of the DSC enclosure. Typically, the sensor is brazed to the enclosure to ensure that heat flows easily and uniformly between the sensor and the enclosure. The sample in a pan 104 is placed on the sensor sample position 105, a reference (if used) in a pan 106 is placed on the sensor reference position 107. Because the sample and reference pans are in direct contact with the DSC sensor, heat flows well between them and the sensor, guaranteeing that very nearly all heat flow to and from the sample and reference is through the sensor, and is therefore measured. The cavity 108 of the DSC enclosure is closed by inner lid 109. Cavity 108 is continuously purged with a purge gas, typically nitrogen (although other gases such as helium or argon may be used).

Because the body of the cavity is fabricated from a single piece of a very high thermal conductivity material (typically silver), its temperature is very uniform. Because inner lid 109 merely rests on surface 110 of enclosure body 103, heat exchange between inner lid 109 and enclosure body 103 is relatively poor. Outer lid 111 completely covers the inner lid 109 and also rests on enclosure body 103 on surface 112, such that inner lid 109 and outer lid 111 do not contact one another. Surrounding the entire upper portion of the DSC enclosure is a thermal insulation enclosure comprising body 113 and removable lid 114 that allows the inner and outer lids of the DSC enclosure to be removed for sample and reference loading and unloading.

Thus adding an outer lid to the DSC enclosure improves temperature uniformity within the DSC enclosure, and substantially reduces errors due to extraneous heat flow.

EXAMPLE 1

Figure 4:
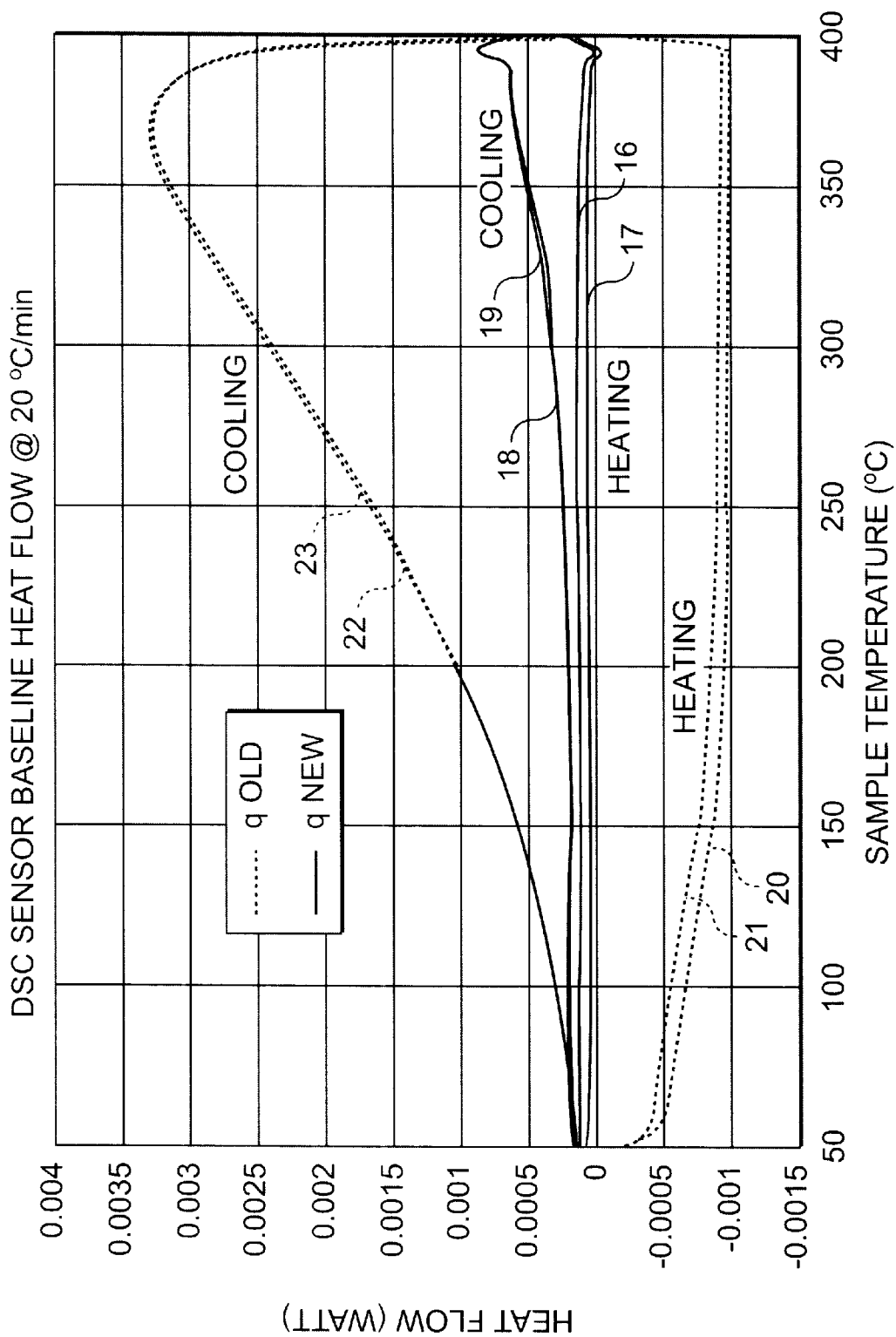
FIG. 4 is a plot showing a comparison between the heat flow measured with an empty cell using the conventional prior art heat flow calculation using only the second term of the heat flow equation and the heat flow measured with an empty cell including all four terms of the heat flow equation.

FIG. 4 shows the heat flow baseline for an empty DSC incorporating the preferred embodiment of the sensor of the present invention, using the conventional single term heat flow equation and the four-term equation with sensor thermal parameters determined using the disclosed method. The thermal program in this example consists of a five-minute isothermal segment at 50° C., a 20° C./min constant heating rate segment to 400° C., a 5 minute isothermal segment at 400° C., and an uncontrolled cool to 50° C. In this example the sensor thermal parameters were fitted using quadratic polynomial equations. Because the DSC cell is empty, ideally, the heat flow should be zero at all times during this experiment. Non-zero heat flow indicates imbalance between the sample and reference sides of the DSC.

Traces 16 and 17 are the empty-cell heat flow curves for two consecutive 20° C./min heating segments using the four-term heat flow equation of the present invention. Traces 20 and 21 are the empty-cell heat flow curves for the same two consecutive 20° C./min heating segments using the prior art single term heat flow equation. Traces 18 and 19 are the empty-cell heat flow curves for uncontrolled cooling to 50° C. at the completion of the 400° C. isothermal segments, using the four-term heat flow equation of the present invention. Traces 22 and 23 are the empty-cell heat flow curves for uncontrolled cooling to 50° C. at the completion of the 400° C. isothermal segments, using the single term heat flow equation. Comparison of the two sets of heat flow curves shows that the four-term heat flow equation using the present invention results in a substantially straighter heat flow baseline that is much closer to zero heat flow at all points, during both heating and cooling, e.g., during heating, the baseline bow is reduced, the slope is reduced and the offset is reduced.

EXAMPLE 2

Figure 5:
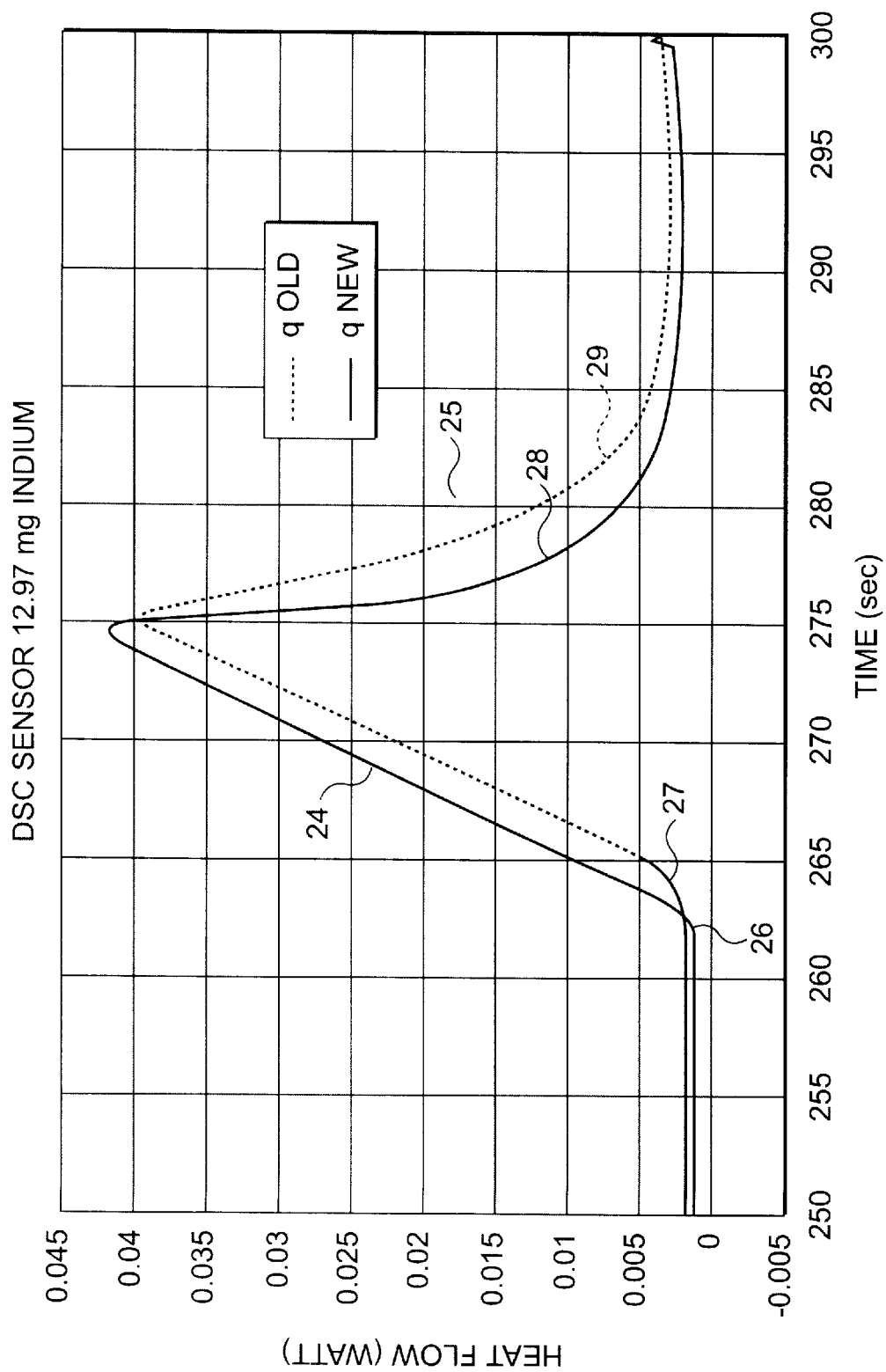
FIG. 5 is a plot showing a comparison between the heat flow measured using a prior art heat flow sensor and the heat flow measured using the present invention where the sample is 12.97 mg of indium.

FIG. 5 shows the heat flow curve for a 12.97 mg indium sample melted during a 20° C./min heating segment for a DSC incorporating the sensor of the present invention. Heat flow is calculated using the four-term equation of the present invention (trace 24) and the conventional single term heat flow equation (trace 25). The sensor thermal parameters were determined using the first preferred method described above, and fitted using quadratic polynomials. Trace 24 is the heat flow curve using the four-term equation, trace 25 is the heat flow curve using the single term equation. The melt onset is the point at which the indium sample begins to melt. At that point, the heat flow to the sample begins to increase. Ideally, the heat flow curve should turn upward sharply when melting commences. However, because of heat transfer effects within the sample, the sample pan, the sensor and the interfaces between them, the heat flow curve is rounded off, or smeared. This smearing reduces the precision with which the temperature of the onset can be determined. The onset temperature is taken as the melting temperature of the sample, which is an important experimental result. Thus, sharper melt onset heat flow curves are more accurate, since they will define the melt temperature more accurately than rounded-off curves. Melt onset 26 of the four-term heat flow curve is clearly much sharper than melt onset 27 of the single term heat flow equation. Notice also that the shape of the melt onset is distinctly different for the four-term heat flow equation than for the single term equation.

During the melt, the heat flow continues to increase until the sample is entirely melted at which point the heat flow to the sample begins to decrease and the heat flow curve decays. If a second transition begins before the heat flow signal has decayed completely, the two transitions are difficult to separate for purposes of determining the integrated peak areas of the two transitions and the onset temperature of the second transition is more difficult to determine. Thus, the speed of the decay of the heat flow signal after the completion of the transition is important, with faster decay preferable. The baseline return 28 of the four-term heat flow signal is clearly much more rapid than baseline return 29 of the single term heat flow signal, as shown in FIG. 5.

To understand why the melt onset heat flow curve appears to be different for the heat flow curve of the present invention as compared to a conventional DSC, the heat flow between the sensor and the sample pan needs to be considered. Heat flowing to the sample flows from the sample side of the sensor to the sample pan through a thermal contact resistance. This heat flow is just equal to $q_s$ from the sample heat balance equation. The heat flow equation for heat flow from the sample sensor to the sample pan is:

$$q_s = \frac{T_s - T_p}{R_p}$$

where $T_p$ is the temperature of the sample pan and $R_p$ is the thermal contact resistance between the sensor and the sample pan.

Figure 6:
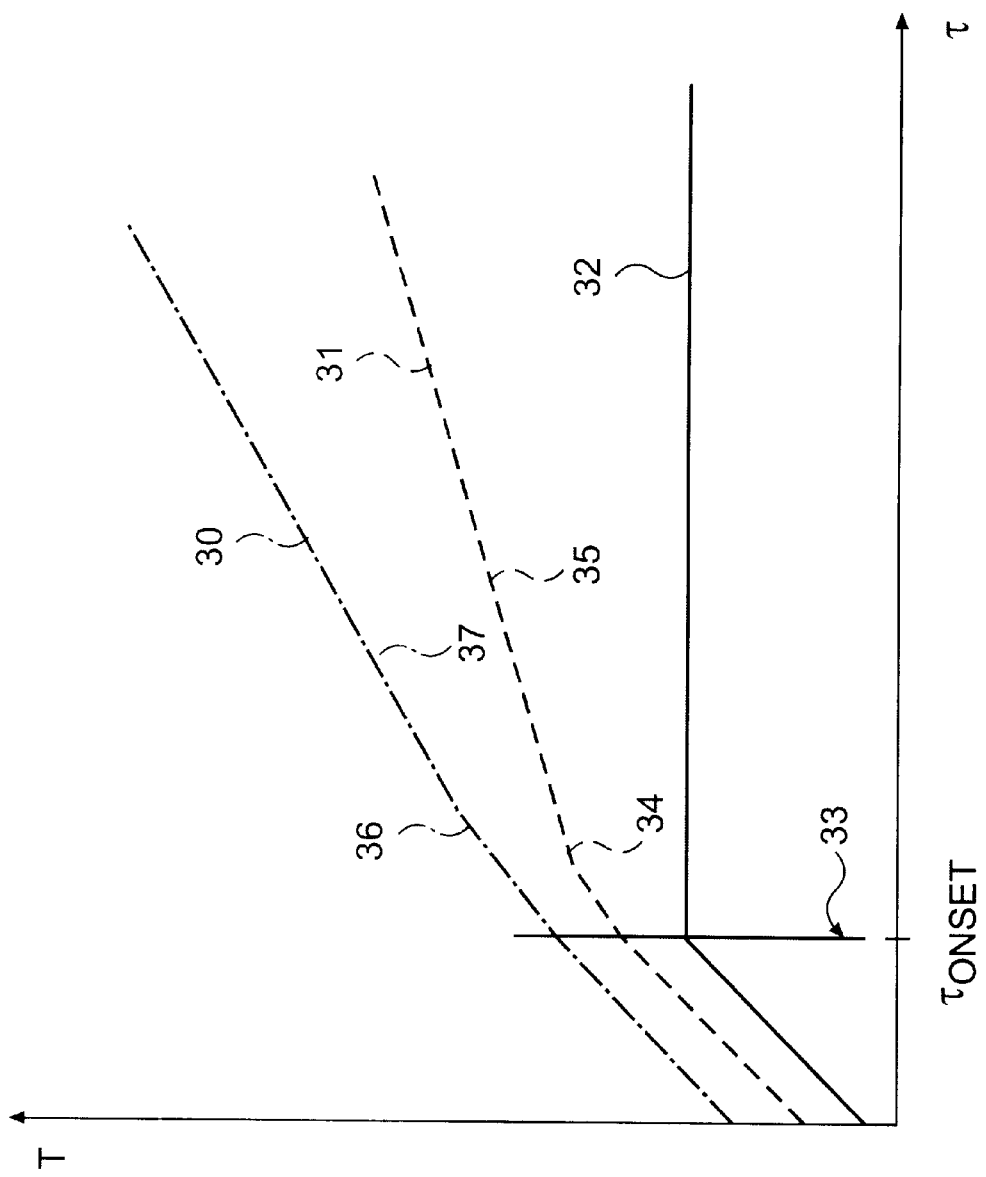
FIG. 6 is a plot showing the temperatures of the sample, sample pan, and sample sensor during the onset of a melt in the present invention.

FIG. 6 is a graphic representation of the temperatures of the sample sensor, the sample pan and the sample, during a time interval surrounding the onset of a melt. Temperature is shown as the ordinate and time is shown as the abscissa. Trace 30 is the sample sensor temperature, trace 31 is the sample pan temperature and trace 32 is the sample temperature. The melt begins at the onset time, $\tau_{onset}$ 33. Before the melt onset, the sample sensor, sample pan and sample temperature traces are parallel, because all three are changing at the heating rate of the DSC, indicating a stationary heat flow. At melt onset 33, the sample temperature stops changing. The sample pan temperature passes through a transient region 34, where the rate of change of temperature decreases until a steady-state condition 35 is established. Here the temperature changes at a constant rate which is slower than the heating rate of the DSC sensor base. Similarly, the sample sensor temperature 30 passes through a transient region 36, where the rate of change of temperature decreases until a steady-state condition 37 is reached, where the rate of change of temperature is slower than that of the DSC sensor base, yet faster than that of the sample pan.

The heat flow to the sample $q_s$ as expressed above is proportional to the difference between sample sensor and sample pan temperatures. At the same time, the reference heat flow $q_r$ is constant. This is because the configuration of the sensor makes the temperatures $T_s$ and $T_r$ independent. Thus, it will be readily seen that the melt onset heat flow 26 given by the four-term heat flow equation shown in FIG. 5 has the correct shape.

The change in the onset shape and the increased speed of the return to baseline following the melt is due principally to the fourth term of the four-term heat flow equation. The fourth term accounts for differing heat storage between the sample and reference side of the sensor as a result of the differing heating rates between the sample and reference sides of the sensor.

Further Calculation

A further calculation that accounts for the heat flows associated with the sample and reference pans is described below. This is a method for calculating the sample heat flow in a Differential Scanning Calorimeter in which the effect of heat storage in the sample pans and the difference in heating rate between sample and reference are included. Accounting for heat flow associated with the pans and the difference between sample and reference heating rate gives a more accurate sample heat flow measurement and improves resolution, which is the ability to separate closely spaced thermal events in the heat flow result.

Differential Scanning Calorimeters measure the heat flow to a sample as the sample temperature is varied in a controlled manner. There are two basic types of DSC, heat flux and power compensation. Brief descriptions of the two types of DSC are included below. For more detailed information on the construction and theory of DSC, see "Differential Scanning Calorimetry an Introduction for Practitioners", G. Höhne, W. Hemminger and H. -J. Flammersheim (Springer-Verlag, 1996).

Heat flux DSCs include a sensor to measure heat flow to a sample to be analyzed. The sensor has a sample position and a reference position. The sensor is installed in an oven whose temperature is varied dynamically according to a desired temperature program. As the oven is heated or cooled, the temperature difference between the sample and reference positions of the sensor is measured. This temperature difference is assumed to be proportional to the heat flow to the sample.

Power compensation DSCs include a sample and a reference holder installed in a constant temperature enclosure. Each of the holders has a heater and a temperature sensor. The average of the sample and reference holder temperatures is used to control temperature, which follows the desired temperature program. In addition, differential power proportional to the temperature difference between the holders is added to the average power to the sample holder and subtracted from the average power to the reference holder in an effort to reduce the temperature difference between sample and reference holders to zero. The differential power is assumed to be proportional to the sample heat flow and is obtained by measuring the temperature difference between the sample and reference holder. In commercial power compensation DSCs, the difference between sample and reference temperature is generally not zero because a proportional controller is used to control the differential power.

A sample to be analyzed is loaded into a pan and placed on the sample position of the DSC. An inert reference material may be loaded into a pan and placed on the reference position of the DSC although usually the reference pan is empty. The temperature program for conventional DSC typically includes combinations of linear temperature ramps and constant temperature segments. Modulated DSC uses a temperature program in which periodic temperature oscillations are superposed on linear ramps and isothermal segments. The experimental result is the sample heat flow versus temperature or time. The heat flow signal is the result of heat flow to or from the sample due to its specific heat and as a result of transitions occurring in the sample.

During the dynamic portion of the DSC experiment, a temperature difference is created between the sample and reference positions of the DSC. In heat flux DSC the temperature difference results from the combination of three differential heat flows. The difference between the sample and reference heat flow, the difference between sample and reference sensor heat flow and the difference between sample and reference pan heat flow. In power compensation DSC the temperature difference results from the combination of three differential heat flows plus the differential power supplied to the sample holders. The differential heat flows are: the difference between the sample and reference heat flow, the difference between sample and reference holder heat flow and the difference between sample and reference pan heat flow. The heat flow difference between the sample and reference consists of heat flow due to the heat capacity difference between the sample and reference, the heat flow of a transition, or the difference in heating rate that occurs during a MDSC experiment. The heat flow difference between the sample and reference sections of the DSC is the result of thermal resistance and capacitance imbalances in the sensor or between the holders and the difference in heating rate that occurs between the sample and reference sections of the DSC during a transition or during a MDSC experiment. Similarly, the heat flow difference between the sample and reference pans is the result of mass differences between the pans and the difference in heating rate that occurs during a sample transition or during a MDSC experiment.

In conventional heat flux DSCs the sensor imbalance and pan imbalance are assumed to be insignificant and the differences in heating rates are ignored. In conventional power compensation DSC the holder imbalance and pan imbalance are assumed to be insignificant and the differences in heating rates are ignored. When the balance assumptions are satisfied and the sample heating rate is the same as the programmed heating rate, the temperature difference is proportional to the sample heat flow and the differential temperature gives an accurate measure of the sample heat flow. The sample heat flow is only proportional to the measured temperature difference between sample and reference when the heating rate of the sample and reference are identical, the sensor is perfectly symmetrical, and the pan masses are identical. Proportionality of sample heat flow to temperature difference for a balanced sensor and pans occurs only during portions of the experiment when the instrument is operating at a constant heating rate, the sample is changing temperature at the same rate as the instrument and there are no transitions occurring in the sample.

During Modulated DSC experiments, the heating rates of the sample and reference are generally not the same and the difference between measured sample and reference temperatures is not proportional to the sample heat flow. Thus, the sample heat flow from a conventional DSC is not the actual sample heat flow, but includes the effects of imbalances and differences in heating rates; in other words the DSC sample heat flow measurement is smeared. For many DSC experiments, the smeared sample heat flow is a sufficiently accurate result. For example, when the desired experimental result is the total energy of the transition, like the heat of fusion of a melt, the total peak area is integrated over a suitable baseline and the result from a conventional DSC is sufficiently accurate. If however, partial integration of the peak area is required (for example in the study of reaction kinetics), the smeared sample heat flow of conventional DSC cannot be used. Another example of when the conventional DSC result is inadequate is when two or more transitions in a sample occur within a small temperature interval. In that case, the transitions may be poorly separated because of the smearing effects. The improvement in resolution obtained by using the present method greatly improves the separation of closely spaced transitions. In any case, the heat flow signal from conventional DSC does not accurately portray the sample heat flow during a transition.

During a transition, the heat flow to the sample increases or decreases from the pre-transition value depending upon whether the transition is exothermic or endothermic and whether the DSC is being heated or cooled. The change in sample heat flow causes the heating rate of the sample to be different from that of the DSC and as a consequence, the sample pan and sensor heating rates become different from the programmed heating rate.

U.S. patent application Ser. No. 09/533,949 (the '949 application), incorporated by reference herein, discloses a heat flux DSC that uses a four term heat flow equation to account for sensor imbalances and differences in heating rate between the sample and reference sections of the sensor. Heat flow results from that invention show improved dynamic response and hence improved resolution along with improvements in the empty DSC cell heat flow. However, the heat flow signal obtained from the practice of that invention still includes the effects of the sample pans.

In a power compensation differential scanning calorimeter, a five term heat flow equation accounts for sample and reference holder imbalances and differences in heating rate between the sample and reference holders. Heat flow results from that invention show improved dynamic response and hence improved resolution along with improvements in the empty DSC cell heat flow. However, the heat flow signal obtained from the practice of that invention still includes the effects of the sample pans.

In summary, this is a method for calculating sample heat flow in a differential scanning calorimeter that accounts for differences in heating rate between the sample and reference pans and the difference in heating rate between the sample and reference (if a reference is used). It may be applied to heat flux or power compensation DSCs, which are able to measure the sample and the reference heat flows independently and which account for imbalances and differences in heating rate between the sample and reference sections of the heat flow measuring apparatus.

Differential scanning calorimeters employing this method furnish a sample heat flow signal that is an accurate representation of the sample heat flow during the entire DSC experiment, free of the smearing effects that are present in conventional DSC. DSCs using this method will have greatly improved resolution. Kinetic analysis requiring partial integration of peak areas can be practiced using this method whereas conventional DSC cannot be used, due to the distortions of the sample heat flow signal.

This is a method for calculating sample heat flow, including the heat flow effects of the sample pans using heat flow signals obtained as described in the patent applications that are incorporated by reference herein. The result is a more accurate measurement of the sample heat flow during transitions when the heating rate of the sample differs from that of the reference. Resolution is improved because the return to baseline of the heat flow signal at the completion of a transformation is much more rapid.

Heat Flux DSCs

Figure 1:
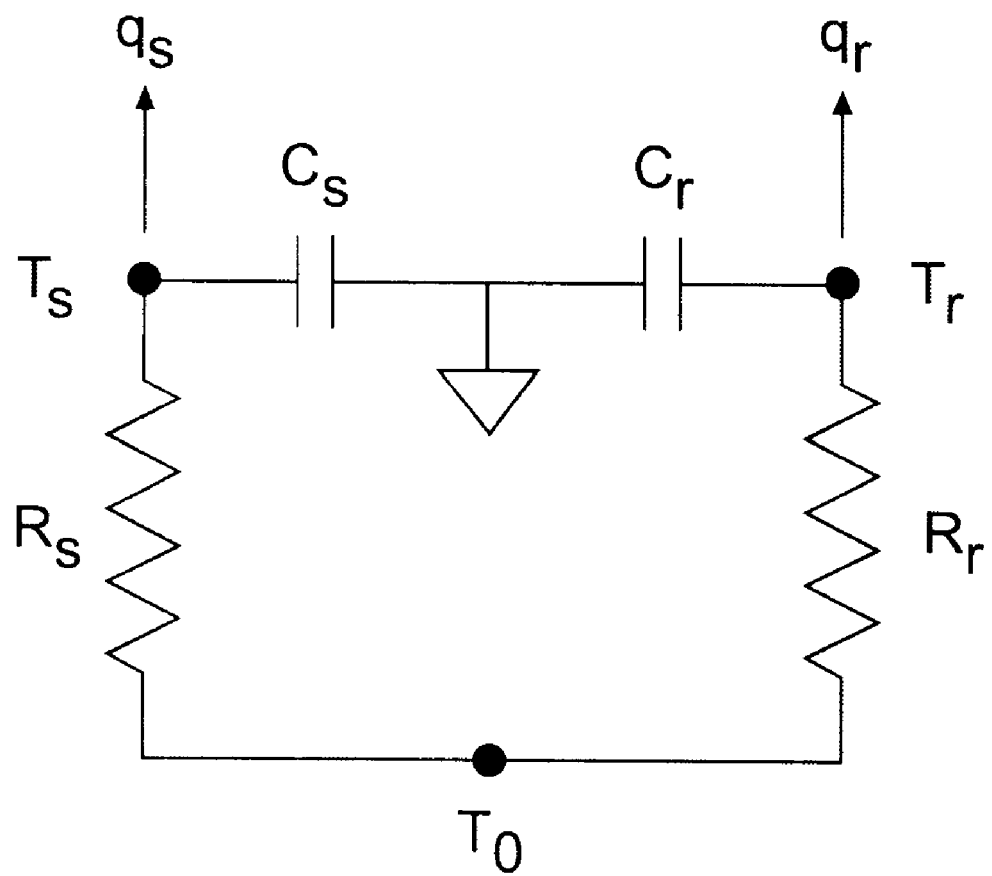
FIG. 1 is a thermal network model of an embodiment of the present invention.

A heat flux DSC sensor according to the invention disclosed in the '949 application comprises independent sample and reference measuring sections that may be modeled using a thermal resistance and a thermal capacitance for each of the sample and reference sections as shown in FIG. 1. Thermal resistance and capacitance elements are idealizations of the sensor, which allow mathematical expressions describing the thermal behavior of the sensor to be written. $R_s$ and $R_r$ are thermal resistances, $C_s$ and $C_r$ are thermal capacitances representing the sample and reference sections of the sensor. $T_o$, $T_s$ and $T_r$ are the temperatures of the sensor base, sample position and reference positions. The heat flow to the sample and its pan and to the reference and its pan are $q_s$ and $q_r$, respectively.

Performing a heat balance on the sample and reference gives the heat flow differential equations.

$$q_s = \frac{T_0 - T_s}{R_s} - C_s \cdot \frac{dT_s}{d\tau}$$

$$q_r = \frac{T_0 - T_r}{R_r} - C_r \cdot \frac{dT_r}{d\tau}$$

In the preferred embodiment of the '949 invention, temperature $T_o$, the difference between the sensor base and sample position temperatures and the difference between the sample and reference position temperatures are measured. The differential temperatures are defined by.

$$\Delta T = T_s - T_r$$

$$\Delta T_o = T_o - T_s$$

Substituting into the heat balance equations gives, $$q_s = \frac{\Delta T_0}{R_s} - C_s \cdot \frac{dT_s}{d\tau} \text{ and}$$

$$q_r = \frac{\Delta T_0 + \Delta T}{R_r} - C_r \cdot \left( \frac{dT_s}{d\tau} - \frac{d\Delta T}{d\tau} \right)$$

Sample temperature is obtained from the definition of $\Delta T_o$, $$T_s = T_o - \Delta T_o$$

Thermal resistances and capacitances of the sensor as a function of temperature are obtained using the calibration method disclosed in the '949 application. Using thermal resistances and capacitances obtained by calibration with the temperatures and differential temperatures measured during a DSC experiment allows the sample and reference heat flows, $q_s$ and $q_r$ to be found. As used in the '949 invention and in conventional DSC, the difference between sample and reference heat flows is the desired result.

$$q = q_s - q_r$$

As noted above, the sample and reference heat flows include the heat flow to the sample and reference and to their pans.

$$q_s = q_{ss} + q_{ps}$$

$$q_r = q_{rs} + q_{pr}$$

Where, $q_{ss}$ is the sample heat flow, $q_{ps}$ is the sample pan heat flow, $q_{rs}$ is the reference heat flow and $q_{rp}$ is the reference pan heat flow. Because the pans and the reference do not have transitions, their heat flows are just the sensible heat associated with their specific heats:

$$q_{ps} = m_{ps} \cdot c_p \cdot \frac{dT_{ps}}{d\tau}$$

$$q_r = m_{pr} \cdot c_p \cdot \frac{dT_{pr}}{d\tau} + m_{rs} \cdot c_{rs} \cdot \frac{dT_{pr}}{d\tau}$$

Where, $m_{ps}$ and $m_{pr}$ are the masses of the sample and reference pans, $c_p$ is the specific heat of the pan material, $m_{rs}$ is the mass of the reference material, $c_{rs}$ is the specific heat of the reference material. The sample pan temperature is $T_{ps}$ and the reference pan temperature is $T_{pr}$. It is assumed that because the reference material has no transitions it heats at the same rate as the reference pan.

Substituting for the sample pan heat flow and solving for the sample heat flow:

$$q_{ss} = q_s - m_{ps} \cdot c_p \cdot \frac{dT_{ps}}{d\tau}$$

Solve the reference heat flow equation for the pan specific heat and substitute it into the sample heat flow equation.

$$q_{ss} = q_s - q_r \cdot \frac{m_{ps}}{m_{pr}} \cdot \frac{\frac{dT_{ps}}{d\tau}}{\frac{dT_{pr}}{d\tau}} + \frac{m_{ps}}{m_{pr}} \cdot m_{rs} \cdot c_{rs} \cdot \frac{dT_{ps}}{d\tau}$$

This equation gives the actual sample heat flow, accounting for the sample and reference pan heat flows and the heat flow to the reference. The second term on the right hand side is seen to be the reference heat flow multiplied by the ratio of the sample and reference pan masses and by the ratio of the sample and reference pan heating rates. It accounts for the fact that during a transition, the sample pan heats at a different rate than the reference pan because of the transition heat flow. The third term accounts for the heat flow to the reference material. In most cases, the reference pan is empty and the sample heat flow equation becomes.

$$q_{ss} = q_s - q_r \cdot \frac{m_{ps} \cdot \frac{dT_{ps}}{d\tau}}{m_{pr} \cdot \frac{dT_{pr}}{d\tau}}$$

When the sample heating rate is different from the reference heating rate, the fraction of reference heat flow subtracted from the sample heat flow is greater or less, depending upon whether the sample pan heating rate is greater or less than that of the reference pan. Because the reference heat flow is just the reference pan heat flow, this equation accounts for differences between sample and reference pan heating rates. For example, during a melt in DSC, the sample pan heating rate falls below the programmed rate, while the reference pan continues to heat at the programmed rate. In a conventional DSC the reference heat flow being subtracted from the sample heat flow is for a pan heating at the programmed rate. Thus, during the melt, too much heat is being subtracted from the sample heat flow and the heat flow signal is too small. During the baseline return, the sample pan is heating faster than the reference pan and insufficient heat flow is subtracted from the sample heat flow. As a consequence, the heat flow signal is too large.

To use the true sample heat flow equation requires that the sample and reference pan temperatures be known so that their derivatives may be taken. Unfortunately there is no way to measure the pan temperatures directly. The pan temperatures can be calculated using the temperature and heat flow signals.

The equations for heat flow from the sensor to the sample and reference pans are:

$$q_s = \frac{T_s - T_{ps}}{R_{ps}}$$

$$q_r = \frac{T_r - T_{pr}}{R_{pr}}$$

Solving for the pan temperatures.

$$T_{ps}=T_s-q_s \cdot R_{ps}$$

$$T_{pr}=T_r-q_r \cdot R_{pr}$$

Using these equations, pan temperatures and sample heat flows can be calculated from the measured signals. A predetermined function is used for the pan thermal resistances. Pan thermal resistance depends on the pan configuration, purge gas used in the DSC and the temperature of the DSC.

It must be noted that the present method cannot be applied to heat flux DSCs generally: the sample and the reference heat flows must be measured separately. The invention disclosed in the '949 application allows the sample and reference heat flows to be measured separately, and is required to apply use the present method.

Power Compensation DSCs

Figure 7:
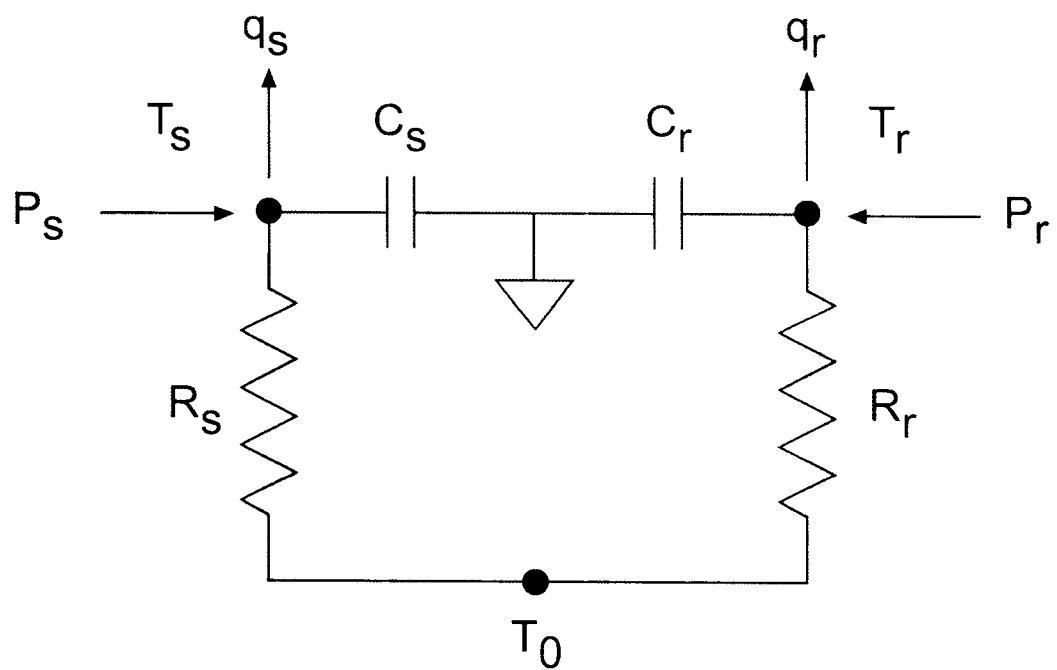
FIG. 7 is a thermal network model of a power compensation differential scanning calorimeter.

A power compensation DSC comprises independent sample and reference holders that may be modeled using a thermal resistance and a thermal capacitance for each of the sample and reference holders as shown in FIG. 7. Thermal resistance and capacitance elements are idealizations of the sample and reference holders, which allow mathematical expressions describing the thermal behavior of the DSC to be written. $R_s$ and $R_r$ are thermal resistances, $C_s$ and $C_r$ are thermal capacitances representing the sample and reference holders. $T_o$, $T_s$ and $T_r$ are the temperatures of the isothermal enclosure, sample holder and reference holder. Heating power supplied to the sample holder is $p_s$, comprising the average heating power plus the differential power. Heating power supplied to the reference holder is $P_r$, comprising the average heating power minus the differential power. The heat flow to the sample and its pan and to the reference and its pan are $q_s$ and $q_r$.

Performing a heat balance on the sample and reference gives the heat flow differential equations, $$q_s = \frac{T_0 - T_s}{R_s} + p_s - C_s \cdot \frac{dT_s}{d\tau}$$

$$q_r = \frac{T_0 - T_r}{R_r} + p_r - C_r \cdot \frac{dT_r}{d\tau}$$

In the preferred embodiment of the '949 invention, temperature $T_o$, the difference between the isothermal enclosure and sample holder temperatures and the difference between the sample and reference holder temperatures are measured. The differential temperatures are defined by:

$$\Delta T = T_s - T_r$$

$$\Delta T_o = T_o - T_s$$

Substituting into the heat balance equations gives, $$q_s = \frac{\Delta T_0}{R_s} + p_s - C_s \cdot \frac{dT_s}{d\tau}$$

and $$q_r = \frac{\Delta T_0 + \Delta T}{R_r} + p_r - C_r \cdot \left(\frac{dT_s}{d\tau} - \frac{d\Delta T}{d\tau}\right)$$

Sample temperature is obtained from the definition of $\Delta T_o$, $$T_s = T_o - \Delta T_o$$

Thermal resistances and capacitances of the sample and reference holders as a function of temperature are obtained using the calibration method disclosed in the '949 invention. Using thermal resistances and capacitances from calibration with the sample and reference holder power, temperatures and differential temperatures measured during a DSC experiment allows the sample and reference heat flow, $q_s$ and $q_r$ to be found. As used in the '949 invention and in conventional DSC, the difference between sample and reference heat flows is the desired result.

$$q = q_s - q_r$$

As noted above, the sample and reference heat flows include the heat flow to the sample and reference and to their pans.

$$q_s = q_{ss} + q_{ps}$$

$$q_r = q_{rs} + q_{pr}$$

Where $q_{ss}$ is the sample heat flow, $q_{ps}$ is the sample pan heat flow, $q_{rs}$ is the reference heat flow and $q_{rp}$ is the reference pan heat flow. The pans and the reference do not have transitions so that their heat flows are just the sensible heat associated with their specific heats:

$$q_{ps} = m_{ps} \cdot c_p \cdot \frac{dT_{ps}}{d\tau}$$

$$q_r = m_{pr} \cdot c_p \cdot \frac{dT_{pr}}{d\tau} + m_{rs} \cdot c_{rs} \cdot \frac{dT_{pr}}{d\tau}$$

Where $m_{ps}$ and $m_{pr}$ are the masses of the sample and reference pans, $c_p$ is the specific heat of the pan material, $m_{rs}$ is the mass of the reference material, $c_{rs}$ is the specific heat of the reference material. The sample pan temperature is $T_{ps}$ and the reference pan temperature is $T_{pr}$. It is assumed that because the reference material has no transitions it heats at the same rate as the reference pan.

Substituting for the sample pan heat flow and solving for the sample heat flow:

$$q_{ss} = q_s - m_{ps} \cdot c_p \cdot \frac{dT_{ps}}{d\tau}$$

Solving the reference heat flow equation for the pan specific heat and substituting it into the sample heat flow equation:

$$q_{ss} = q_s - q_r \cdot \frac{m_{ps}}{m_{pr}} \cdot \frac{\frac{dT_{ps}}{d\tau}}{\frac{d_{pr}}{d\tau}} + \frac{m_{ps}}{m_{pr}} \cdot m_{rs} \cdot c_{rs} \cdot \frac{dT_{ps}}{d\tau}$$

This equation gives the actual sample heat flow, accounting for the sample and reference pan heat flows and the heat flow to the reference. The second term on the right hand side is seen to be the reference heat flow multiplied by the ratio of the sample and reference pan masses and by the ratio of the sample and reference pan heating rates. It accounts for the fact that during a transition, the sample pan heats at a different rate than the reference pan because of the transition heat flow. The third term accounts for the heat flow to the reference material. In most cases, the reference pan is empty and the sample heat flow equation becomes.

$$q_{ss} = q_s - q_r \cdot \frac{m_{ps} \cdot \frac{dT_{ps}}{d\tau}}{m_{pr} \cdot \frac{dT_{pr}}{d\tau}}$$

When the sample heating rate is different from the reference heating rate, the fraction of reference heat flow subtracted from the sample heat flow is greater or less, depending upon whether the sample pan heating rate is greater or less than that of the reference pan. Because the reference heat flow is just the reference pan heat flow, this equation accounts for differences between sample and reference pan heating rates. For example, during a melt in DSC, the sample pan heating rate falls below the programmed rate, while the reference pan continues to heat at the programmed rate. In a conventional DSC the reference heat flow being subtracted from the sample heat flow is for a pan heating at the programmed rate thus, during the melt too much heat is being subtracted from the sample heat flow and the heat flow signal is too small. During the baseline return, the sample pan is heating faster than the reference pan and insufficient heat flow is subtracted from the sample heat flow, consequently the heat flow signal is too large.

To use the true sample heat flow equation requires that the sample and reference pan temperatures be known so that their derivatives may be taken. Unfortunately there is no way to measure the pan temperatures directly. The pan temperatures can be calculated using the temperature and heat flow signals.

The equations for heat flow from the sample and reference holders to the sample and reference pans are:

$$q_s = \frac{T_s - T_{ps}}{R_{ps}} \quad q_r = \frac{T_r - T_{pr}}{R_{pr}}$$

Solving for the pan temperatures:

$$T_{ps} = T_s - q_s \cdot R_{ps}$$

$$T_{pr} = T_r - q_r \cdot R_{pr}$$

Using these equations, the pan temperatures and sample heat flows are obtained from measurements. A predetermined function is used for the pan thermal resistances. Pan thermal resistance depends on the pan configuration, purge gas used in the DSC and the temperature of the DSC.

It must be noted that the present method cannot be applied to power compensation DSCs generally. The sample and the reference heat flows must be measured separately. The invention disclosed in the power compensation continuation-in-part application to the '949 application referenced above allows the sample and reference heat flows to be measured separately and is required to practice the present method.

Experimental Results

Figure 8:
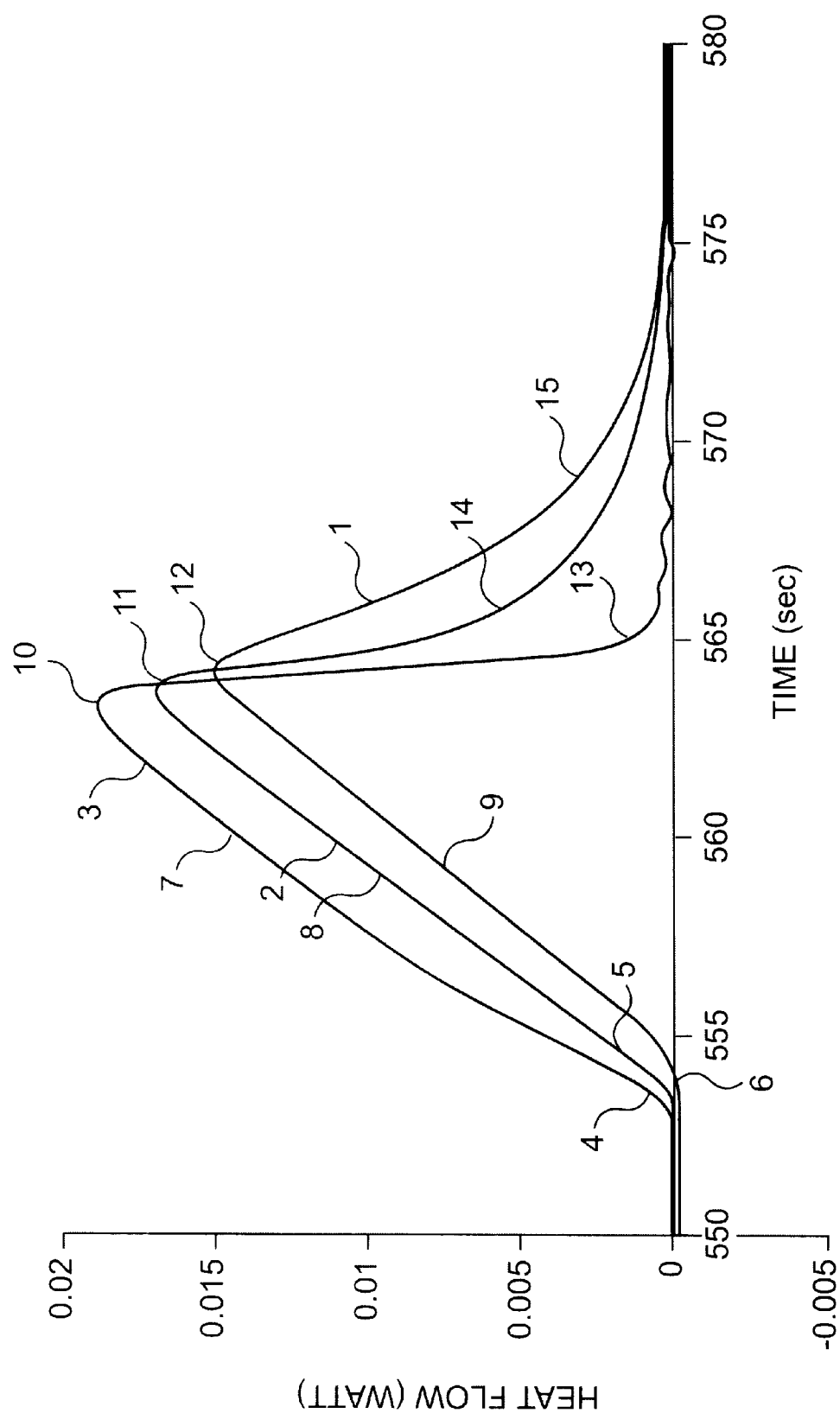
FIG. 8 is a plot showing a comparison of the heat flow obtained using the further calculation to the heat flow obtained using conventional DSCs, and to the heat flow obtained using the invention summary section.

FIG. 8 shows the calculation of DSC heat flows in a heat flux DSC, for a 4.92 mg indium melt at 10° C./min plotted versus time, using the further calculation. The conventional DSC result is the curve labeled 1, the result using the invention described in the summary section is labeled 2 and the result using the further calculation is labeled 3. Beginning at the left side of the plot, the onset of the indium melt for the further calculation method 4 occurs earlier and is steeper than the onset of indium that occurs using the invention described in the summary section 5, or using a conventional DSC 6. During the melt, the heat flow signal of the present method 7 is much larger than that obtained using the invention described in the summary section 8, which in turn is substantially larger than the signal obtained using conventional DSC 9. The melt is completed at the heat flow signal peak when the latent heat of fusion has been absorbed by the sample.

Also, the heat flow peak of the method using the further calculation 10 is higher and occurs slightly earlier compared to the peak of the invention described in the summary section 11, and much higher and earlier still than the peak obtained using a conventional DSC 12. Immediately following the peak, the sample heat flow decreases rapidly as the flow of heat to the sample following the melt returns to the value just before the transition which, corresponds to the specific heat of the sample. The post melt decay of the heat flow signal 13 of the calculated using the further calculation is extremely rapid, while the post melt heat flow decay 14 of the invention described in the summary section is much slower and the post melt decay 15 of conventional DSC is slower still. The complete indium melt heat flow signal 3 of the method using the further calculation comprising the onset 4, melt 7, peak heat flow 10 and post melt decay 13 is a more accurate measurement than that of the invention in the summary section described in or of a conventional DSC.

The various features of the present invention can be used either singularly or in many different combinations.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A sensor in an oven of a heat flux differential scanning calorimeter comprising:
    (a) an absolute temperature detector which measures one of a base temperature, a sample temperature and a reference temperature as an absolute temperature;
    (b) a first differential temperature detector which measures one of the difference between the sample temperature and the base temperature, the difference between the reference temperature and the base temperature and the difference between the sample temperature and the reference temperature as a first differential temperature;
    (c) a second differential temperature detector which measures another one of the difference between the sample temperature and the reference temperature, the difference between the sample temperature and the base temperature and the difference between the reference temperature and the base temperature as a second differential temperature;
    wherein the base temperature is measured directly or is determined from at least one of the absolute temperature, the first differential temperature and the second differential temperature;

wherein the base temperature is used to control the power to the oven; and wherein the sensor is calibrated by running a first experiment with a first calibration set, said first calibration set comprising a first sample calibration sample on a sample position of the differential scanning calorimeter and a first reference calibration sample on a reference position of the differential scanning calorimeter, and then running a second experiment with a second calibration set comprising a second sample calibration sample on the sample position of the differential scanning calorimeter and a second reference calibration sample on the reference position of the differential scanning calorimeter.

2. The sensor of claim 1, wherein the first calibration set is a null calibration set, such that the first experiment is run with an empty differential scanning calorimeter cell.

3. The sensor of claim 2, wherein the sample position is a sample platform mounted on a thin-walled cylinder.

4. The sensor of claim 2, wherein a time constant for the sample and a time constant for the reference are determined from the first experiment according to:

$$\tau_s = \frac{\Delta T_o}{\left(\frac{dT_s}{d\tau}\right)}$$

$$\tau_r = \frac{\Delta T_o + \Delta T}{\left(\frac{dT_s}{d\tau}\right) - \left(\frac{d\Delta T}{d\tau}\right)}$$

respectively.

5. The sensor of claim 2, wherein a sensor sample thermal capacitance is determined from the second experiment and is given by:

$$C_s = \frac{m_s \cdot C_{mat}}{\frac{\Delta T_o}{\left(\frac{dT_s}{d\tau}\right) \cdot \tau_s} - 1}$$

wherein $m_s$ is the mass of the second sample calibration sample and $C_{mat}$ is the known specific heat of the second sample calibration sample.

6. The sensor of claim 5, wherein a sensor reference thermal capacitance is determined from the second experiment and is given by $$C_r = \frac{m_r \cdot C_{mat}}{\frac{\Delta T_o + \Delta T}{\left(\frac{dT_s}{d\tau} - \frac{d\Delta T}{d\tau}\right) \cdot \tau_r} - 1}$$

wherein $m_r$ is the mass of the second reference calibration sample and $C_{mat}$ is the known specific heat of the second reference calibration sample.

7. The sensor of claim 6, wherein a sample thermal resistance is calculated from $R_s = \tau_s/C_s$ and the reference thermal resistance is calculated from $R_r = \tau_r/C_r$.

8. The sensor of claim 1, wherein, of the base temperature, the sample temperature and the reference temperature, the absolute temperature detector measures the base temperature as the absolute temperature.

9. The sensor of claim 8, wherein the first differential temperature detector measures the difference between the sample temperature and the base temperature.

10. The sensor of claim 9, wherein the second differential temperature detector measures the difference between the sample temperature and the reference temperature.

11. The sensor of claim 1, wherein the sensor has a sample thermal capacitance and a sample thermal resistance and the sample thermal capacitance and the sensor sample thermal resistance are calculated from:

$$C_s = \frac{\Delta T_{o1} \cdot q_{s2} - \Delta T_{o2} \cdot q_{s1}}{\Delta T_{o2} \frac{dT_{s1}}{d\tau} - \Delta T_{o1} \frac{d\Delta T_{s2}}{d\tau}}$$

$$R_s = \frac{\Delta T_{o2} \cdot \frac{dT_{s1}}{d\tau} - \Delta T_{o1} \cdot \frac{dT_{s2}}{d\tau}}{q_{s2} \cdot \frac{dT_{s1}}{d\tau} - q_{s1} \cdot \frac{dT_{s2}}{d\tau}}.$$

12. The sensor of claim 11, wherein the sensor reference thermal capacitance and the sensor reference thermal resistance are calculated from:

$$R_r = \frac{(\Delta T_{o2} + \Delta T_2) \cdot \left(\frac{dT_{s1}}{d\tau} - \frac{d\Delta T_1}{d\tau}\right) - (\Delta T_{o1} + \Delta T_1) \cdot \left(\frac{dT_{s2}}{d\tau} - \frac{d\Delta T_2}{d\tau}\right)}{q_{r2} \cdot \left(\frac{dT_{s1}}{d\tau} - \frac{d\Delta T_1}{d\tau}\right) - q_{r1} \cdot \left(\frac{dT_{s2}}{d\tau} - \frac{d\Delta T_2}{d\tau}\right)}$$

$$C_r = \frac{(\Delta T_{o1} + \Delta T_1) \cdot q_{r2} - (\Delta T_{o2} + \Delta T_2) \cdot q_{r1}}{(\Delta T_{o2} + \Delta T_2) \cdot \left(\frac{dT_{s1}}{d\tau} - \frac{d\Delta T_1}{d\tau}\right) - (\Delta T_{o1} + \Delta T_1) \cdot \left(\frac{dT_{s2}}{d\tau} - \frac{d\Delta T_2}{d\tau}\right)}.$$

13. The sensor of claim 1, wherein the first calibration set is a null calibration set such that the first experiment is run with an empty differential scanning calorimeter cell, and wherein the sample calibration sample and the reference calibration sample are sapphire samples.

14. A sensor for an oven of a heat flux differential scanning calorimeter comprising:

(a) an absolute temperature detector measuring a base temperature at a base of the sensor;

(b) a first differential temperature detector measuring the difference between a sample temperature at a sample position and the base temperature;

(c) a second differential temperature detector measuring the difference between the sample temperature and a reference temperature at a reference position;

wherein the sensor is calibrated by running a first experiment with an empty differential scanning calorimeter cell and a second experiment with a sample calibration sample in the sample position and a reference calibration sample in the reference position.

15. The sensor of claim 14, wherein the sample calibration sample and the reference calibration sample are sapphire samples.

16. The sensor of claim 14, wherein a time constant for the sample and a time constant for the reference are determined from the first experiment according to:

$$\tau_s = \frac{\Delta T_o}{\left(\frac{dT_s}{d\tau}\right)}$$

$$\tau_r = \frac{\Delta T_o + \Delta T}{\left(\frac{dT_s}{d\tau}\right) - \left(\frac{d\Delta T}{d\tau}\right)}$$

respectively.

17. The sensor of claim 16, wherein the sensor has a sensor thermal capacitance and the sensor sample thermal capacitance is determined from the second experiment and is given by:

$$C_s = \frac{m_s \cdot C_{mat}}{\frac{\Delta T_o}{\left(\frac{dT_s}{d\tau}\right) \cdot \tau_s} - 1}$$

wherein $m_s$ is the mass of the sample calibration sample and $C_{mat}$ is the known specific heat of the sample calibration sample.

18. The sensor of claim 17, wherein the sensor has a reference thermal capacitance and the sensor reference thermal capacitance is determined from the second experiment and is given by $$C_r = \frac{m_r \cdot C_{mat}}{\frac{\Delta T_o + \Delta T}{\left(\frac{dT_s}{d\tau} - \frac{d\Delta T}{d\tau}\right) \cdot \tau_r} - 1}$$

wherein $m_r$ is the mass of the reference calibration sample and $C_{mat}$ is the known specific heat of the reference calibration sample.

19. The sensor of claim 18, wherein the sample thermal resistance is calculated from $R_s = \tau_s/C_s$ and the reference thermal resistance is calculated from $R_r = \tau_r/C_r$.

20. The sensor of claim 14, wherein the sample position is a sample platform mounted on a thin-walled cylinder.

21. A method for calibrating a sensor for a heat flux differential scanning calorimeter having an absolute temperature measurement detector, a first differential temperature measurement detector and a second differential temperature measurement detector comprising:

(a) placing a first sample calibration sample on a sample position of the differential scanning calorimeter and a first reference calibration sample on a reference position of the differential scanning calorimeter;

(b) running a first experiment comprising a first isothermal segment, a second constant heating rate segment and a third isothermal segment, and measuring an absolute temperature with the absolute temperature detector, a first differential temperature using the first differential temperature measurement detector and a second differential temperature using the second differential temperature measurement detector;

(c) placing a second sample calibration sample on a sample position of the differential scanning calorimeter and a second reference calibration sample on a reference position of the differential scanning calorimeter;

(d) running a second experiment comprising the first isothermal segment, the second constant heating rate segment and the third isothermal segment, and measuring the absolute temperature with the absolute temperature detector, the first differential temperature using the first differential temperature measurement detector and the second differential temperature using the second differential temperature measurement detector; and (e) calculating the sensor sample thermal resistance, the sensor reference thermal resistance, the sensor sample thermal capacitance and the sensor reference thermal capacitance, wherein the sensor is calibrated by calculating the sensor sample thermal resistance, the sensor reference thermal resistance, the sensor sample thermal capacitance and the sensor reference thermal capacitance.

22. The method of claim 21, wherein the sensor sample thermal capacitance and the sensor sample thermal resistance are calculated according to $$C_s = \frac{\Delta T_{o1} \cdot q_{s2} - \Delta T_{o2} \cdot q_{s1}}{\Delta T_{o2} \frac{dT_{s1}}{d\tau} - \Delta T_{o1} \frac{d\Delta T_{s2}}{d\tau}}$$

$$R_s = \frac{\Delta T_{o2} \cdot \frac{dT_{s1}}{d\tau} - \Delta T_{o1} \cdot \frac{dT_{s2}}{d\tau}}{q_{s2} \cdot \frac{dT_{s1}}{d\tau} - q_{s1} \cdot \frac{dT_{s2}}{d\tau}}.$$

23. The method of claim 22, wherein the sensor reference thermal capacitance and the sensor reference thermal resistance are calculated according to $$R_r = \frac{(\Delta T_{o2} + \Delta T_2) \cdot \left(\frac{dT_{s1}}{d\tau} - \frac{d\Delta T_1}{d\tau}\right) - (\Delta T_{o1} + \Delta T_1) \cdot \left(\frac{dT_{s2}}{d\tau} - \frac{d\Delta T_2}{d\tau}\right)}{q_{r2} \cdot \left(\frac{dT_{s1}}{d\tau} - \frac{d\Delta T_1}{d\tau}\right) - q_{r1} \cdot \left(\frac{dT_{s2}}{d\tau} - \frac{d\Delta T_2}{d\tau}\right)}$$

$$C_r = \frac{(\Delta T_{o1} + \Delta T_1) \cdot q_{r2} - (\Delta T_{o2} + \Delta T_2) \cdot q_{r1}}{(\Delta T_{o2} + \Delta T_2) \cdot \left(\frac{dT_{s1}}{d\tau} - \frac{d\Delta T_1}{d\tau}\right) - (\Delta T_{o1} + \Delta T_1) \cdot \left(\frac{dT_{s2}}{d\tau} - \frac{d\Delta T_2}{d\tau}\right)}.$$

24. A method for operating a heat flux differential scanning calorimeter having a sensor comprising an absolute temperature measurement detector for measuring the temperature of a base position on the sensor, a first differential temperature detector for measuring the temperature difference between a sample position and the base position, and a second differential temperature detector for measuring the temperature difference between a reference position and the sample position, comprising:

(a) the step of calibrating the sensor; and (b) operating the differential scanning calorimeter.

25. The method of claim 24, wherein the step of calibrating the sensor comprises a first experiment with an empty differential scanning calorimeter cell.

26. The method of claim 25, wherein the step of calibrating the sensor comprises a second experiment using a sample calibration sample having mass $m_s$ and a reference calibration sample having mass $m_r$.

27. The method of claim 24, wherein the step of calibrating the sensor uses a sapphire sample calibration sample and a sapphire reference calibration sample.

28. The method of claim 24, wherein the step of calibrating the sensor comprises calculating sensor sample and reference time constants.

29. The method of claim 24, wherein the sensor has a sample thermal capacitance and wherein the step of calibrating the sensor comprises calculating the sensor sample thermal capacitance according to:

$$C_s = \frac{m_s \cdot Cmat}{\frac{\Delta T_o}{\left(\frac{dT_s}{d\tau}\right) \cdot \tau_s} - 1}$$

30. The method of claim 24, wherein the sensor has a reference thermal capacitance and wherein the step of calibrating the sensor comprises calculating the sensor reference thermal capacitance according to:

$$C_r = \frac{m_r \cdot C_{mat}}{\left[\frac{\Delta T_o + \Delta T}{\left(\frac{dT_s}{d\tau} - \frac{d\Delta T}{d\tau}\right) \cdot \tau_r} - 1\right]}$$

31. A method for calibrating a sensor for a heat flux differential scanning calorimeter having an absolute temperature measurement detector, a first differential temperature measurement detector and a second differential temperature measurement detector comprising:

(a) running a first experiment comprising a first isothermal segment, a second constant heating rate segment and a third isothermal segment with an empty differential scanning calorimeter cell, and measuring a first differential temperature using the first differential temperature measurement detector and a second differential temperature using the second differential temperature measurement detector;

(b) placing a sample calibration sample on a sample position of the differential scanning calorimeter and a reference calibration sample on a reference position of the differential scanning calorimeter;

(c) running a second experiment comprising a fourth isothermal segment, a fifth constant heating rate segment and a sixth isothermal segment, and simultaneously measuring the first differential temperature using the first differential temperature measurement detector and the second differential temperature using the second differential temperature measurement detector; and (d) calculating a sensor sample thermal resistance, a sensor reference thermal resistance, a sensor sample thermal capacitance and a sensor reference thermal capacitance.

32. The method of claim 31, wherein the heating rate for the fifth constant heating rate segment is equal to the heating rate for the second constant heating rate segment.

33. The method of claim 31, further comprising calculating a time constant for the sample position and a time constant for the reference position according to:

$$\tau_s = \frac{\Delta T_o}{\left(\frac{dT_s}{d\tau}\right)}$$

$$\tau_r = \frac{\Delta T_o + \Delta T}{\left(\frac{dT_s}{d\tau}\right) - \left(\frac{d\Delta T}{d\tau}\right)}$$

respectively.

34. The method of claim 33, wherein the sample thermal capacitance is calculated from:

$$C_s = \frac{m_s \cdot C_{mat}}{\left[\frac{\Delta T_o}{\left(\frac{dT_s}{d\tau}\right) \cdot \tau_s} - 1\right]}$$

wherein $m_s$ is the mass of the second sample calibration sample and $C_{mat}$ is the known specific heat of the second sample calibration sample.

35. The method of claim 34, wherein the sensor reference thermal capacitance is calculated from:

$$C_r = \frac{m_r \cdot C_{mat}}{\left[\frac{\Delta T_o + \Delta T}{\left(\frac{dT_s}{d\tau} - \frac{d\Delta T}{d\tau}\right) \cdot \tau_r} - 1\right]}$$

wherein $m_r$ is the mass of the second reference calibration sample and $C_{mat}$ is the known specific heat of the second reference calibration sample.

36. The method of claim 35, wherein the sample thermal resistance is calculated from $R_s = \tau_s/C_s$ and the reference thermal resistance is calculated from $R_r = \tau_r/C_r$.

37. A sensor for a heat flux differential scanning calorimeter comprising:

(a) a sample platform mounted on the top of a sample cylindrical tube, said tube having a cylindrical wall thickness;

(b) a reference platform mounted on the top of a reference cylindrical tube, said tube having a cylindrical wall thickness;

(c) a base attached to the bottom of the sample cylindrical tube and the bottom of the reference cylindrical tube; and (d) a base thermocouple for measuring an absolute temperature at a base position on the base, a first differential thermocouple configuration for measuring a sample/base differential temperature at the sample platform with respect to the base, and a second differential thermocouple configuration for measuring a sample/reference differential temperature at the sample platform with respect to the reference platform.

38. The sensor of claim 37, wherein the height of the sample and reference cylindrical tubes is selected to increase the sensitivity of the sensor.

39. The sensor of claim 37, wherein the height of the sample and reference cylindrical tubes is selected to increase the resolution of the sensor.

40. The sensor of claim 37, wherein the sample cylindrical tube has an aspect ratio and wherein the aspect ratio of the sample cylinder is between 25 and 35 inches$^{-1}$.

41. The sensor of claim 37, wherein the sample and reference cylindrical tubes are made of constantan.

42. The sensor of claim 37, wherein the first differential thermocouple configuration comprises an area detector welded concentrically to the underside of the sample platform.

43. The sensor of claim 37, wherein the height of the sample cylindrical tube is between 0.02 and 0.5 inches.

44. A method for calibrating a heat flux differential scanning calorimeter having a base temperature detector measuring the temperature at a base position, a first differential temperature detector measuring the temperature difference between a sample position and the base position, and a second differential temperature detector measuring the temperature difference between the sample position and reference position comprising:

(a) running a first experiment comprising a first isothermal segment, a second constant heating rate segment and a third isothermal segment with an empty differential scanning calorimeter cell, and measuring a first differential temperature using the first differential temperature measurement detector and a second differential temperature using the second differential temperature measurement detector;

(b) placing a sample calibration sample on a sample position of the differential scanning calorimeter and a reference calibration sample on a reference position of the differential scanning calorimeter;

(c) running a second experiment comprising a fourth isothermal segment, a fifth constant heating rate segment and a sixth isothermal segment, and simultaneously measuring the first differential temperature using the first differential temperature measurement detector and the second differential temperature using the second differential temperature measurement detector; and (d) calculating a sensor sample thermal resistance, a sensor reference thermal resistance, a sensor sample thermal capacitance and a sensor reference thermal capacitance, wherein the differential scanning calorimeter is calibrated by calculating the sensor sample thermal resistance, the sensor reference thermal resistance, the sensor sample thermal capacitance and the sensor reference thermal capacitance.

45. The method of claim 44, wherein step (d) further comprises calculating a sample time constant and a reference time constant.

46. The method of claim 45, wherein the sample thermal capacitance is calculated from:

$$C_s = \frac{\frac{m_s \cdot C_{mat}}{\Delta T_o}}{\left(\frac{dT_s}{d\tau}\right) \cdot \tau_s} - 1$$

wherein $m_s$ is the mass of the sample calibration sample and $C_{mat}$ is the known specific heat of the sample calibration sample.

47. The method of claim 45, wherein the sensor reference thermal capacitance is calculated from:

$$C_r = \frac{\frac{m_r \cdot C_{mat}}{\Delta T_o + \Delta T}}{\left(\frac{dT_s}{d\tau} - \frac{d\Delta T}{d\tau}\right) \cdot \tau_r} - 1$$

wherein $m_r$ is the mass of the second reference calibration sample and $C_{mat}$ is the known specific heat of the second reference calibration sample.

48. A calorimeter having an oven, a sample position and a reference position comprising:

(a) an absolute temperature detector which measures one of a base temperature, a sample temperature and a reference temperature as an absolute temperature;

(b) a first differential temperature detector which measures one of the difference between the sample temperature and the base temperature, the difference between the reference temperature and the base temperature and the difference between the sample temperature and the reference temperature as a first differential temperature; and (c) a second differential temperature detector which measures another one of the difference between the sample temperature and the reference temperature, the difference between the sample temperature and the base temperature and the difference between the reference temperature and the base temperature as a second differential temperature;

wherein the base temperature is measured directly or is determined from at least one of the absolute temperature, the first differential temperature and the second differential temperature, wherein the base temperature is used to control power to the oven, and wherein the sample position is effectively independent from the reference position.

49. The calorimeter of claim 48, wherein the sample position comprises a sample platform attached to a thin wall cylindrical tube.

50. The calorimeter of claim 49, wherein the thin wall cylindrical tube is attached to a base.

51. The calorimeter of claim 50, wherein the base, the thin wall cylindrical tube and the platform are made of constantan.

52. The calorimeter of claim 50, wherein the absolute temperature detector is a base temperature detector, and wherein the base temperature detector is attached to the center of a surface of the base.

53. The calorimeter of claim 50, wherein the first differential temperature detector comprises a sample area temperature detector attached to the sample platform.

54. The calorimeter of claim 48, wherein the calorimeter comprises an inner lid and an outer lid, said inner lid enclosing a cavity comprising the sample position and the reference position.

55. A method of calibrating a calorimeter having a reference position and a sample position for a predetermined operating temperature range comprising the steps of:

(a) running a first experiment with nothing on the sample position or on the reference position, said first experiment comprising the steps of:

(i) sensing at least one absolute temperature and two differential temperatures;

(ii) maintaining a steady temperature below the operating temperature range;

(iii) heating the calorimeter at a first constant heating rate to a temperature above the predetermined operating range;

(iv) determining at least one time constant;

(b) running a second experiment with a calibration sample on at least one of the sample position and the reference position comprising the steps of:

(i) sensing at least one absolute temperature and two differential temperatures;

(ii) maintaining a steady temperature below the operating temperature range;

(iii) heating the calorimeter at a second constant heating rate to a temperature above the predetermined operating range; and (iv) determining at least one capacitance and at least one resistance, wherein the calorimeter is calibrated by determining the at least one time constant, the at least one capacitance and the at least one resistance.

56. The method of claim 55, wherein the second experiment comprises placing a sample calibration sample on the sample position and a reference calibration sample on the reference position.

57. The method of claim 56, wherein the sample and reference calibration samples are sapphire calibration samples.

58. The method of claim 55, wherein the time constant determined in the first experiment is the sample time constant and it is determined in step a(iv) according to:

$$\tau_s = \frac{\Delta T_o}{\left(\frac{dT_s}{d\tau}\right)}.$$

59. The method of claim 58, wherein the capacitance determined in the second experiment is the sample thermal capacitance and the sample thermal capacitance is determined in step b(iv) according to:

$$C_s = \frac{m_s \cdot Cmat}{\frac{\Delta T_o}{\left(\frac{dT_s}{d\tau}\right) \cdot \tau_s} - 1}$$

60. The method of claim 55, wherein the steady temperature in step (a)(ii) is maintained for a sufficiently long period of time to permit equilibration of the calorimeter.

61. A method of calibrating a calorimeter having an oven, a reference position and a sample position for a predetermined operating temperature range comprising the steps of:
  (a) running a first experiment with a sample calibration sample on the sample position and a reference calibration sample on the reference position, said first experiment comprising the steps of:
    (i) sensing an absolute temperature and two differential temperatures;
    (ii) maintaining a steady temperature below the predetermined operating temperature range;
    (iii) heating the calorimeter at a first constant heating rate to a temperature above the predetermined operating range;
    (iv) determining at least one time constant of the reference and sample time constants;
  (b) running a second experiment with the sample calibration sample on the sample position and the reference calibration sample on the reference position comprising the steps of:
    (i) sensing an absolute temperature and two differential temperatures;
    (ii) maintaining a steady temperature below the predetermined operating temperature range;
    (iii) heating the calorimeter at a second constant heating rate to a temperature above the predetermined operating range; and
    (iv) determining at least one sensor capacitance and at least one sensor resistance,
  wherein the first constant heating rate differs substantially from the second constant heating rates and wherein the calorimeter is calibrated by determining the at least one time constant, the at least one sensor capacitance and the at least one sensor resistance.

62. The method of claim 61, wherein the second constant heating rate is at least about twice as high as the first constant heating rate.

63. The method of claim 61, wherein the sample and reference calibration samples are sapphire calibration samples.

64. The method of claim 61, further comprising controlling power to the oven based upon the absolute temperature.

65. The method of claim 61, wherein the at least one time constant, the at least one thermal resistance and the at least one thermal capacitance are determined based upon the following four-term heat flow equation:

$$q = \Delta T_0 \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}.$$

66. A method for reducing relative errors in absolute temperature measurements due to differences in temperature sensors used in a heat flux differential scanning calorimeter containing a sample position, a reference position, and a base, the method comprising the steps of:
  (a) measuring a temperature of the base;
  (b) measuring a differential temperature between the sample position and the base;
  (c) measuring a differential temperature between the sample position and the reference position;
  (d) determining at least one time constant, at least one thermal resistance and at least one thermal capacitance based upon a four-term heat flow equation, and
  (e) using the at least one time constant, at least one thermal resistance and at least one thermal capacitance to reduce the relative errors in absolute temperature measurements.

67. The method of claim 66, wherein the method provides a temperature deviation at the sample position for an indium sample placed on the reference position of less than about 1.5% of a second temperature deviation at the sample position for an indium sample placed on the sample position.

68. The method of claim 66, wherein measuring the temperature of the base comprises taking a single absolute temperature measurement.

69. The method of claim 66, wherein measuring the differential temperature measurement between the sample position and the base comprises using a sample area temperature detector.

70. The method of claim 66, wherein measuring the differential temperature measurement between the sample position and the reference position comprises using a reference area temperature detector.

71. The method of claim 66, wherein a temperature of the sample position is determined by subtracting the differential temperature between the sample position and the base from the temperature of the base.

72. A heat flux differential scanning calorimeter comprising:
  (a) a base having a base top side and a base underside;
  (b) a sample cylindrical tube attached to the base top side;
  (c) a reference cylindrical tube attached to the base top side;
  (d) a sample platform mounted on top of the sample cylindrical tube, the sample platform having a sample platform top side and a sample platform underside;
  (e) a reference platform mounted on top of the reference cylindrical tube, the reference platform having a reference platform top side and a reference platform underside;
  (f) a sample area temperature detector attached to the sample platform underside, wherein the sample area temperature detector is thermoelectrically positive;
  (g) a reference area temperature detector attached to the reference platform underside, wherein the reference area temperature detector is thermoelectrically positive; and
  (h) a thermocouple attached to the base, wherein the thermocouple has a positive element and a negative element,
  wherein the differential scanning calorimeter measures a $\Delta T$ voltage between the sample area temperature detector and the reference area temperature detector,
  wherein the differential scanning calorimeter measures a $\Delta T_o$ voltage between the sample area temperature detector and the positive element of the thermocouple, and wherein the differential scanning calorimeter measures a $T_o$ voltage between the positive element and the negative element.

73. The heat flux differential scanning calorimeter of claim 72, wherein a $T_s$ voltage of the sample platform is obtained by combining the $T_o$ voltage with the $\Delta T_s$ voltage.

74. The heat flux differential scanning calorimeter of claim 72, wherein the area temperature detector and the reference temperature detector are circular disks of chromel to which chromel wires are welded.

75. The heat flux differential scanning calorimeter of claim 72, wherein the sample area temperature detector is welded to the sample platform underside at a plurality of places spaced in a circular pattern concentric to the sample area temperature detector and the sample platform.

76. The heat flux differential scanning calorimeter of claim 72, wherein the differential scanning calorimeter comprises an inner lid and an outer lid, said inner lid enclosing a cavity comprising the sample position and the reference position.

77. A calorimeter having a sample position and a reference position comprising:
(a) an absolute temperature detector which obtains an absolute temperature measurement by measuring one of a base temperature, a sample temperature and a reference temperature;
(b) a first differential temperature detector which obtains a first differential temperature measurement by measuring one of the difference between the sample temperature and the base temperature, the difference between the reference temperature and the base temperature and the difference between the sample temperature and the reference temperature; and
(c) a second differential temperature detector which obtains a second differential temperature measurement by measuring another one of the difference between the sample temperature and the reference temperature, the difference between the sample temperature and the base temperature and the difference between the reference temperature and the base temperature, wherein the calorimeter determines the heat flow to the sample from the absolute temperature detector measurement, the first differential temperature detector measurement and the second differential temperature detector measurement, and wherein the sample position is effectively independent from the reference position.

78. The calorimeter of claim 77 wherein the sample position comprises a sample platform attached to a thin wall cylindrical tube.

79. The calorimeter of claim 78 wherein the thin wall cylindrical tube is attached to a base.

80. The calorimeter of claim 79, wherein the base, the thin wall cylindrical tube and the platform are made of constantan.

81. The calorimeter of claim 79, wherein the absolute temperature detector is a base temperature detector, and wherein the base temperature detector is attached to the center of a surface of the base.

82. The calorimeter of claim 79, wherein the first differential temperature detector comprises a sample area temperature detector attached to the sample platform.

83. The calorimeter of claim 79, wherein the calorimeter comprises an inner lid and an outer lid, said inner lid enclosing a cavity comprising the sample position and the reference position.

* * * * *